United States Patent [19]

Karanewsky et al.

[11] Patent Number: 4,616,005
[45] Date of Patent: Oct. 7, 1986

[54] PHOSPHONYL HYDROXYACYL AMINO ACID DERIVATIVES AS ANTIHYPERTENSIVES

[75] Inventors: Donald S. Karanewsky, East Windsor; Edward W. Petrillo, Jr., Pennington, both of N.J.

[73] Assignee: E. R. Squibb & Sons, Inc., Princeton, N.J.

[21] Appl. No.: 809,630

[22] Filed: Dec. 16, 1985

Related U.S. Application Data

[60] Continuation-in-part of Ser. No. 764,449, Aug. 12, 1985, abandoned, which is a division of Ser. No. 608,752, May 10, 1984, abandoned, which is a division of Ser. No. 391,884, Jun. 23, 1984, Pat. No. 4,452,790.

[51] Int. Cl.$^4$ .................. A61K 31/66; A61K 31/675; C07F 9/40; C07F 9/64
[52] U.S. Cl. ........................................ 514/80; 514/89; 514/92; 514/94; 514/95; 514/99; 514/100; 514/119; 546/22; 548/112; 548/119; 548/414; 549/6; 549/218; 549/220; 549/222; 558/171; 558/179
[58] Field of Search ............... 260/942; 546/22; 548/112, 119, 414; 549/6, 218, 220, 222; 514/80, 89, 92, 94, 95, 99, 100, 119; 558/171, 179

[56] References Cited

U.S. PATENT DOCUMENTS

| | | | |
|---|---|---|---|
| 4,053,651 | 10/1977 | Ondetti et al. | 424/319 |
| 4,105,776 | 8/1978 | Ondetti et al. | 424/274 |
| 4,127,359 | 11/1978 | Krapcho | 424/274 |
| 4,129,566 | 12/1978 | Ondetti et al. | 546/326 |
| 4,151,172 | 4/1979 | Ondetti et al. | 260/326.2 |
| 4,154,935 | 5/1979 | Ondetti et al. | 546/189 |
| 4,168,267 | 9/1979 | Petrillo | 260/326.2 |
| 4,192,878 | 3/1980 | Ondetti | 424/270 |
| 4,199,512 | 4/1980 | Ondetti et al. | 260/326.12 |
| 4,234,489 | 11/1980 | Ondetti et al. | 260/326.42 |
| 4,256,761 | 3/1981 | Suh et al. | 424/282 |
| 4,296,033 | 10/1981 | Petrillo et al. | 260/326.2 |
| 4,296,113 | 10/1981 | Ondetti | 424/246 |
| 4,303,583 | 12/1981 | Kim et al. | 424/200 |
| 4,316,896 | 2/1982 | Thorsett et al. | 424/200 |
| 4,337,201 | 6/1982 | Petrillo, Jr. | 548/413 |
| 4,374,131 | 2/1983 | Petrillo, Jr. | 424/200 |
| 4,379,146 | 4/1983 | Greenlee et al. | 424/127 |
| 4,381,297 | 4/1983 | Karanewsky et al. | 424/200 |
| 4,452,790 | 6/1984 | Karanewsky et al. | 424/200 |
| 4,483,850 | 11/1984 | Patchett et al. | 424/177 |

FOREIGN PATENT DOCUMENTS

| | | | |
|---|---|---|---|
| 868532 | 10/1978 | Belgium . | |
| 0009183 | 4/1980 | European Pat. Off. | 424/200 |
| 2027025 | 2/1980 | United Kingdom . | |
| 2028327 | 3/1980 | United Kingdom . | |
| 2039478 | 8/1980 | United Kingdom . | |

OTHER PUBLICATIONS

Galardy, "Inhibition of Angiotensin . . . " Biochem. Biophs. Res. Comm., 1980, vol. 97, pp. 94–99.
Mauger, "Analogs and Homologs of Proline . . . ", Chem. Review, vol. 66, pp. 47–86 (1966).
Thorsett et al., "Phosphorus Containing Inhibitors . . . ", 182 National Meeting, ACS, New York, Aug. 1981, MEDI-7.
Petrillo, Jr., et al., Peptides: Structure and Function, Proceedings of the Eighth American Peptide Symposium, edited by Hruby, et al., Pierce Chemical Co. (1983), pp. 541–550.

*Primary Examiner*—Richard L. Raymond
*Attorney, Agent, or Firm*—Lawrence S. Levinson; Burton Rodney

[57] ABSTRACT

Phosphonyl hydroxyacyl amino acids of the formula

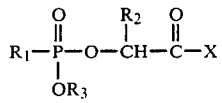

wherein X is a substituted or unsubstituted imino or amino acid or ester. These compounds possess angiotensin converting enzyme activity and are thus useful as hypotensive agents.

21 Claims, No Drawings

PHOSPHONYL HYDROXYACYL AMINO ACID DERIVATIVES AS ANTIHYPERTENSIVES

REFERENCE TO OTHER APPLICATIONS

This application is a continuation-in-part of application Ser. No. 764,449, filed Aug. 12, 1985, now abandoned, which is a division of U.S. application Ser. No. 608,752, filed May 10, 1984, now abandoned which is a division of U.S. application Ser. No. 391,884, filed June 23, 1984, now U.S. Pat. No. 4,452,790.

BACKGROUND OF THE INVENTION

Thorsett, et al in U.S. Pat. No. 4,316,896 disclose phosphoryl derivatives of aminoacids including proline. These compounds are disclosed as being hypotensive agents due to their angiotensin converting enzyme inhibition activity.

Petrillo in U.S. Pat. No. 4,168,267 discloses that various phosphinylalkanoyl substituted prolines are useful as hypotensive agents due to their ability to inhibit the angiotensin converting enzyme.

Ondetti et al in U.S. Pat. No. 4,151,172 disclose that various phosphonoacyl prolines are useful as hypotensive agents due to their ability to inhibit the angiotensin converting enzyme.

Mercaptoacyl derivatives of proline and substituted prolines are known to be useful hypotensive agents due to their angiotensin converting enzyme inhibition activity. Ondetti et al in U.S. Pat. No. 4,105,776 disclose such compounds wherein the proline ring is unsubstituted or substituted by an alkyl or hydroxy group. Ondetti et al. in U.S. Pat. No. 4,154,935 disclose such compounds wherein the proline ring is substituted with one or more halogens. Ondetti et al in U.K. patent application No. 2,028,327 disclose such compounds wherein the proline ring is substituted by various ethers and thioethers. Krapcho in U.S. Pat. No. 4,217,359 discloses such compounds wherein the proline ring has a carbamoyloxy substituent. Krapcho in U.K. patent application No. 2,039,478 discloses compounds wherein the proline ring has a diether, dithioether, ketal or thioketal substituent in the 4-position. Krapcho in U.S. Serial No. 164,985, filed July 1, 1980, now U.S. Pat. No. 4,316,905, discloses such compounds wherein the proline ring has a cycloalkyl, phenyl, or phenyllower alkylene substituent. Ondetti et al in U.S. Pat. No. 4,234,489 disclose such compounds wherein the proline has a keto substituent in the 5-position. Krapcho et al in U.S. Ser. No. 162,341, filed June 23, 1980, now U.S. Pat. No. 4,310,461 disclose such compounds wherein the proline has an imido, amido, or amino substituent in the 4-position. Iwao et al in U.K. patent application No. 2,027,025 disclose such compounds wherein the proline has an aromatic substituent in the 5-position. Ondetti et al in U.S. Pat. Nos. 4,053,651 and 4,199,512 disclose that mercaptoacyl derivatives of various aminoacids other than proline are also useful angiotensin converting enzyme inhibitors.

Karanewsky and Petrillo in U.S. Ser. No. 289,671, now abandoned, disclose phosphonamidate substituted amine or imino acids.

Mercaptoacyl derivatives of 3,4-dehydroproline are disclosed as angiotension converting enzyme inhibitors by Ondetti in U.S. Pat. No. 4,129,566. Mercaptoacyl derivatives of thiazolidinecarboxylic acid and substituted thiazolidinecarboxylic acid are disclosed as angiotensin converting enzyme inhibitors by Ondetti in U.S. Pat. No. 4,192,878 and by Yoshitomo Pharmaceutical Ind. in Belgian Patent No. 868,532.

SUMMARY OF THE INVENTION

This invention is directed to new phosphonate substituted amino or imino acids of formula I and salts thereof

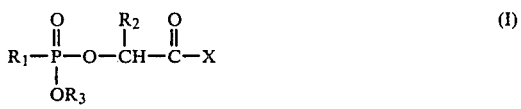

X is an imino or amino acid of the formula

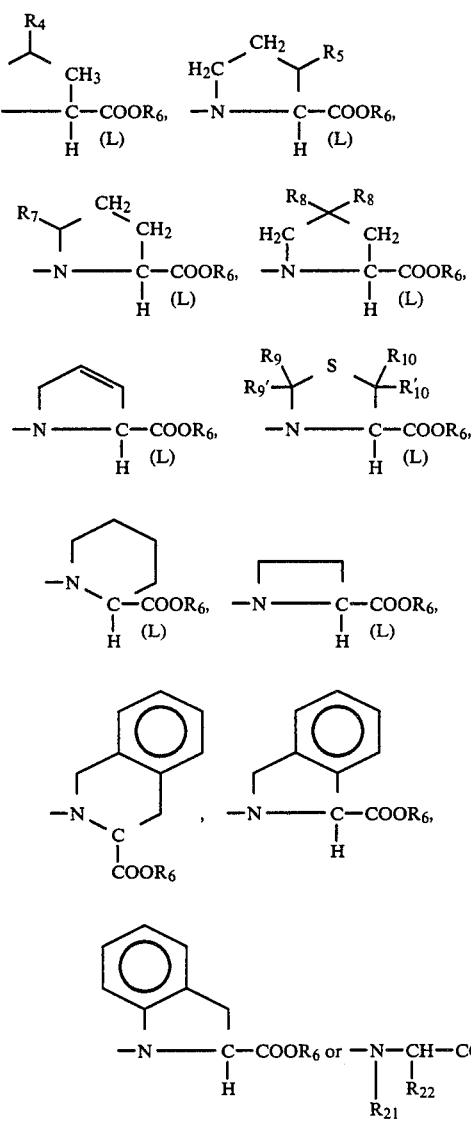

R₄ is hydrogen, lower alkyl, halogen, keto, hydroxy,

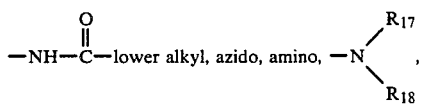

-continued

—NH—C(=O)—(CH₂)ₘ—⟨phenyl⟩(R₁₂)ₚ ,

—(CH₂)ₘ—⟨phenyl⟩(R₁₁)ₚ , —(CH₂)ₘ—⟨furyl, O⟩ ,

—(CH₂)ₘ—⟨thienyl, S⟩ , —(CH₂)ₘ—⟨pyridyl, N⟩ , a 1- or 2-naphthyl of the formula

—(CH₂)ₘ—⟨naphthyl⟩(R₁₂)ₚ,

—(CH₂)ₘ—cycloalkyl, —O—C(=O)—N(R₁₃)(R₁₃), —O—lower alkyl,

—O—(CH₂)ₘ—⟨phenyl⟩(R₁₁)ₚ , a 1- or 2-naphthyloxy of the formula

—O—(CH₂)ₘ—⟨naphthyl⟩(R₁₂)ₚ, —S—lower alkyl,

—S—(CH₂)ₘ—⟨phenyl⟩(R₁₁)ₚ , or a 1- or 2-naphthylthio of the formula

—S—(CH₂)ₘ—⟨naphthyl⟩(R₁₂)ₚ.

R₅ is keto, halogen,

—O—C(=O)—N(R₁₃)(R₁₃), —O—(CH₂)ₘ—⟨phenyl⟩(R₁₁)ₚ ,

—O—lower alkyl, a 1- or 2-naphthyloxy of the formula

—O—(CH₂)ₘ—⟨naphthyl⟩(R₁₂)ₚ,

—S—lower alkyl, —S—(CH₂)ₘ—⟨phenyl⟩(R₁₁)ₚ , or a 1- or 2-naphthylthio of the formula —S—(CH₂)ₘ—⟨naphthyl⟩(R₁₂)ₚ.

R₇ is keto or

—(CH₂)ₘ—⟨phenyl⟩(R₁₁)ₚ .

Each $R_8$ is independently halogen or —Y—$R_{14}$.
$R_9$, $R_9'$, $R_{10}$ and $R_{10}'$ are independently selected from hydrogen and lower alkyl or $R_9'$, $R_{10}$ and $R_{10}'$ are hydrogen and $R_9$ is —⟨phenyl⟩(R₁₂)ₚ

$R_{11}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

$R_{12}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy.

m is zero, one, two or three.

p is one, two or three provided that p is more than one only if $R_{11}$ or $R_{12}$ is hydrogen, methyl, methoxy, chloro, or fluoro.

$R_{13}$ is hydrogen or lower alkyl of 1 to 4 carbons.

Y is oxygen or sulfur.

$R_{14}$ is lower alkyl of 1 to 4 carbons,

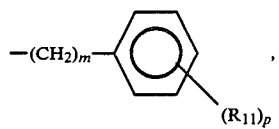

or the $R_{14}$ groups join to complete an unsubstituted 5- or 6-membered ring or said ring in which one or more of the carbons has a lower alkyl of 1 to 4 carbons or a di(lower alkyl of 1 to 4 carbons) substituent.

$R_{21}$ is hydrogen, lower alkyl, cycloalkyl, phenyl, or

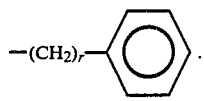

$R_{22}$ is hydrogen, lower alkyl,

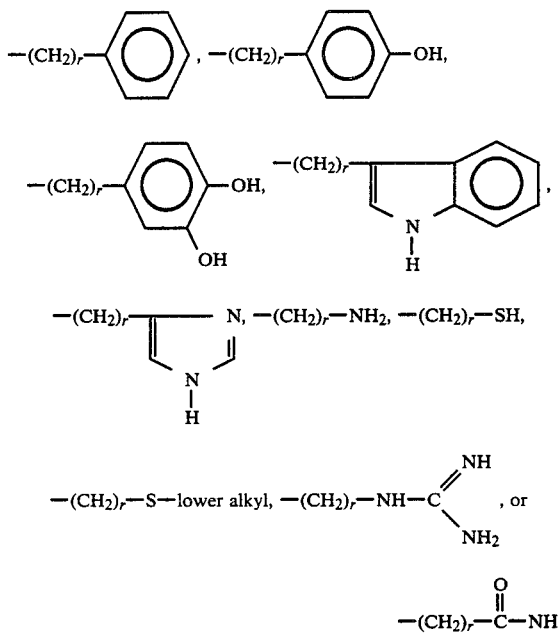

r is an integer from 1 to 4.

$R_1$ is alkyl of 1 to 10 carbons, aminoalkyl, haloalkyl,

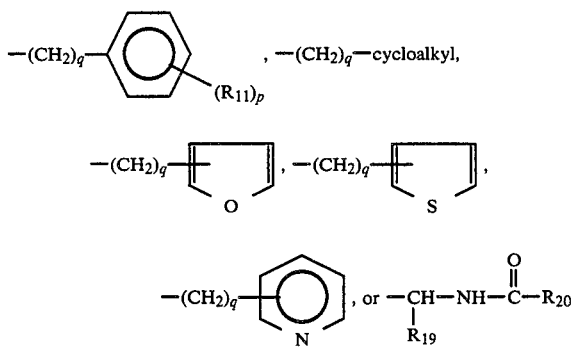

wherein q is zero or an integer from 1 to 7 and $R_{12}$ and p are as defined above.

$R_{19}$ and $R_{20}$ are independently selected from hydrogen, lower alkyl, halo substituted lower alkyl,

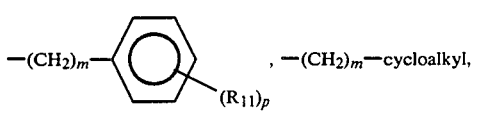

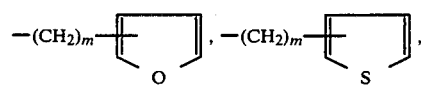

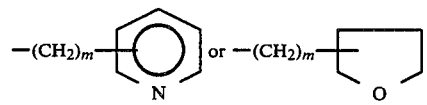

wherein m, $R_{11}$, and p are as defined above.

$R_2$ is hydrogen, lower alkyl, halo substituted lower alkyl,

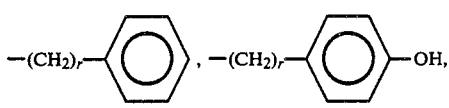

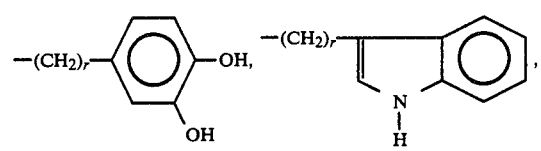

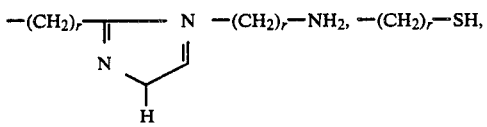

wherein r is as defined above.

$R_3$ and $R_6$ are independently selected from hydrogen, lower alkyl, benzyl, alkali metal such as Li, Na or K, benzhydryl, or

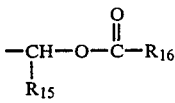

wherein $R_{15}$ is hydrogen, lower alkyl, cycloalkyl, or phenyl, and $R_{16}$ is hydrogen, lower alkyl, lower alkoxy, phenyl, or $R_{15}$ and $R_{16}$ taken together are —(CH$_2$)$_2$—, —(CH$_2$)$_3$—, —CH=CH—, or

$R_{17}$ is lower alkyl, benzyl, or phenethyl.

$R_{18}$ is hydrogen, lower alkyl, benzyl or phenethyl.

DETAILED DESCRIPTION OF THE INVENTION

This invention in its broadest aspects relates to the phosphonate substituted imino or amino acid compounds of formula I above, to compositions containing such compounds and to the method of using such compounds as anti-hypertensive agents.

The term alkyl used in defining $R_1$ refers to straight or branched chain hydrocarbon radicals having up to ten carbons, for example, methyl, ethyl, propyl, isopropyl, butyl, isobutyl, t-butyl, pentyl, isopentyl, heptyl, octyl, decyl, etc. The term lower alkyl used in defining various symbols refers to straight or branched chain radicals having up to seven carbons. The preferred lower alkyl groups are up to four carbons with methyl and ethyl most preferred. Similarly the terms lower alkoxy and lower alkylthio refer to such lower alkyl groups attached to an oxygen or sulfur.

The term cycloalkyl refers to saturated rings of 3 to 7 carbon atoms with cyclopentyl and cyclohexyl being most preferred.

The term halo refers to Cl, Br and F.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc. Similarly, the term amino substituted lower alkyl refers to lower alkyl groups in which one or more hydrogens have been replaced by —NH$_2$, i.e., aminomethyl, 2-aminoethyl, etc.

The symbols

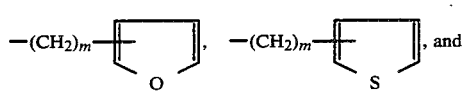

represent that the alkylene bridge is attached to an available carbon atom.

The compounds of formula I wherein $R_1$ is other than

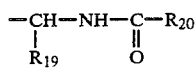

are prepared according to the following procedures. A phosphonic acid of formula II

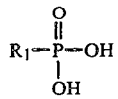

II wherein $R_1$ is as defined above is treated with a chlorinating agent such as phosphorus pentachloride in the presence of an inert organic solvent such as benzene to form a compound of the formula

III which is reacted with a lactate of the formula

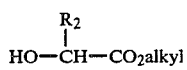

IV in the presence of an organic base such as triethylamine followed by an alcohol $R_3OH$ (where $R_3$ is lower alkyl, benzyl, or benzhydryl) to form a compound of the formula

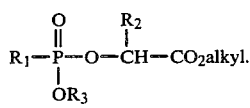

V

The formula V compound is then treated with strong base such as sodium hydroxide or lithium hydroxide in a mixture of water and an organic solvent such as dioxane to form the corresponding acid

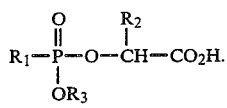

VI

The acid VI or its activated form is then coupled with an imino or amino acid or ester of the formula H—X     VII.

The term activated form refers to the conversion of the acid to a mixed anhydride, symmetrical anhydride, acid chloride, or activated ester, see Methoden der Organischen Chemie (Houben-Weyl), Vol. XV, part II, page 1 et seq. (1974) for a review of the methods of acylation. Preferably the reaction is performed in the presence of a coupling agent such as 1,1-carbonyldiimidazole, thionyl chloride, or dicyclohexylcarbodiimide.

In the above reaction if $R_2$ is

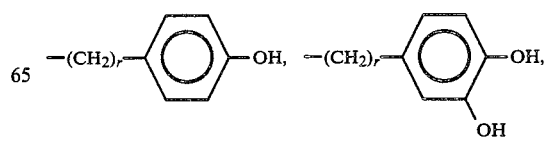

—(CH₂)ᵣ—NH₂, 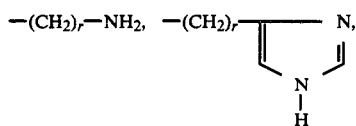

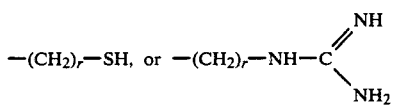

then the hydroxyl, amino, imidazolyl, mercaptan, or guanidinyl function should be protected during the coupling reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or other known methods following completion of the reaction.

Similarly, if in the above reaction $R_1$=aminoalkyl, then the amino group should be similarly protected, preferably by phthalidyl. The protecting group is removed by treatment with hydrazine following completion of the reaction.

The products of formula I wherein either or both of $R_3$ and $R_6$ are lower alkyl, benzyl, or benzhydryl can be hydrogenated, for example, by treating with hydrogen in the presence of a palladium on carbon catalyst or chemically treated such as with sodium hydroxide in aqueous dioxane or with trimethylsilylbromide in dichloromethane to yield the products of formula I wherein $R_3$ and $R_6$ are hydrogen.

The ester products of formula I wherein $R_6$ is

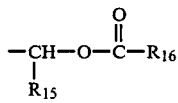

may be obtained by employing the imino or amino acid of formula V in the above reactions with the ester group already in place. Such ester reactants can be prepared by treating peptide, imino, or amino acids with an acid chloride such as

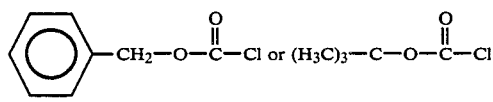

so as to protect the N-atom. The protected acid compound is then reacted in the presence of base with a compound of the formula

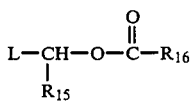    VIII wherein L is a leaving group such as chlorine, bromine, tolylsulfonyloxy, etc., followed by removal of the N-protecting group such as by treatment with acid or hydrogenation.

The ester products of formula I wherein $R_6$ is

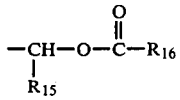

can also be obtained by treating the product of formula I wherein $R_6$ is hydrogen with a molar equivalent of the compound of formula VIII. The diester products wherein $R_3$ and $R_6$ are the same and are

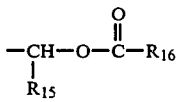

can be obtained by treating the product of formula I wherein $R_3$ and $R_6$ are both hydrogen or an alkali metal salt with two or more equivalents of the compound of formula VIII.

The ester products of formula I wherein $R_3$ is

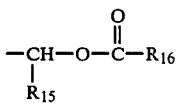

can be obtained by treating the product of formula I wherein $R_3$ is hydrogen or an alkali metal salt and $R_6$ is benzyl or benzhydryl with the compound of formula VIII in the presence of base. Removal of the $R_6$ ester group such as by hydrogenation yields the products of formula I wherein $R_3$ is

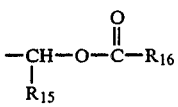

and $R_6$ is hydrogen.

The products of formula I wherein $R_4$ is amino may be obtained by reducing the corresponding products of formula I wherein $R_4$ is azido.

The various imino and amino acids and esters of formula V are described in the literature and in the various patents and pending U.S. application referred to above. Various substituted prolines are also disclosed by Mauger et al., Chem. Review, Vol. 66, p. 47–86 (1966). When the amino or imino acid is known, it can be readily converted to the ester by conventional means. For example, the esters where $R_6$ is t-butyl can be obtained by treating the corresponding N-carbobenzyloxyimino acid with isobutylene under acidic conditions and then removing the N-carbobenzyloxy protecting group by catalytic hydrogenation and the esters wherein $R_6$ is benzyl can be obtained by treating the imino acid with benzyl alcohol and thionyl chloride.

As disclosed by Krapcho in U.S. Ser. No. 164,985, now abandoned, the substituted prolines wherein

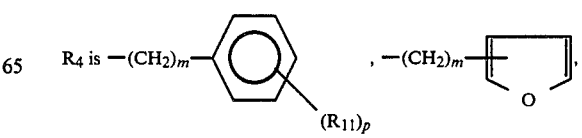

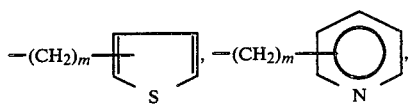 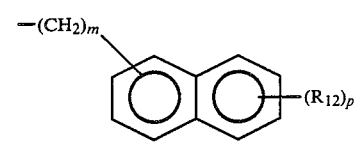

or —(CH$_2$)$_m$-cycloalkyl are prepared by reacting a 4-keto proline of the formula

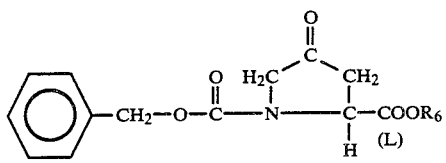 IX with a solution of the Grignard or lithium reagent

   R$_4$—Mg-halo or R$_4$—Li   X wherein R$_4$ is as defined above and halo is Br or Cl to yield

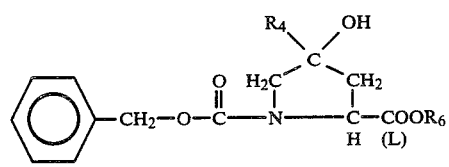 XI

This compound is treated with a dehydrating agent such as p-toluenesulfonic acid, sulfuric acid, potassium bisulfate, or trifluoroacetic acid to yield the 3,4-dehydro-4-substituted proline of the formula

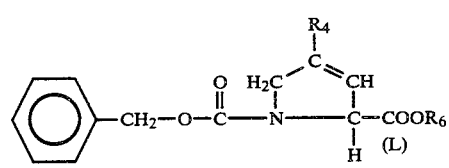 XII

Removal of the N-benzyloxycarbonyl protecting group and hydrogenation of the compound of formula XII yields the desired starting materials. The substituted proline wherein R$_4$ is cyclohexyl can be prepared by further hydrogenation of the 4-phenyl proline compound.

The substituted prolines wherein R$_4$ is the substituted amino group

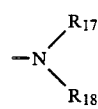

may be prepared by reacting a 4-keto proline of formula IX with the amine

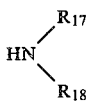

in the presence of hydrogen and catalyst or in the presence of sodium cyanotrihydridoborate.

The compounds of formula I wherein R$_1$ is

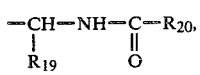

that is

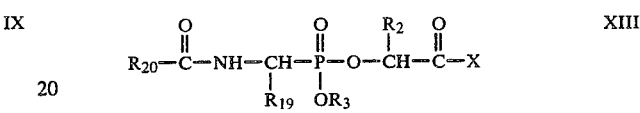 XIII may be prepared by reacting an aminophosphonic acid of the formula

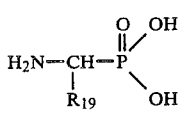 XIV with an acid chlorine having the formula

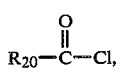 XV such as benzoyl chloride, in the presence of an inert organic solvent, such as dioxane and a weak organic base, such as triethylamine to yield

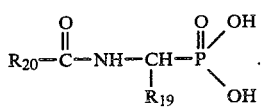 XVI

The formula XVI compound is then coupled with an imino or amino acid or ester of formula XVII

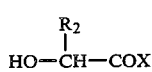 XVII in the presence of a coupling agent, such as dicyclohexylcarbodiimide as described above to form

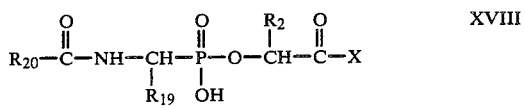 XVIII

Where X includes a protecting group, it may be removed by hydrogenation wherein the protecting group is phenylmethoxycarbonyl or by treatment with hydrazine where the protecting group is phthalidyl to yield the compounds of formula XIII.

The compounds of formula XVII may be prepared by coupling a hydroxy acid of formula XIX as the free acid or corresponding sodium salt

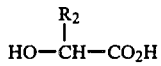   XIX with an imino or amino ester of formula VII preferably in the presence of a coupling agent such as diphenyl phosphorylazide.

Preferred compounds of this invention with respect to the amino or imino acid or ester part of the structure of formula I are those wherein:

$R_{21}$ is hydrogen, methyl, phenyl, cyclopentyl or cyclohexyl;

$R_{22}$ is hydrogen, lower alkyl of 1 to 4 carbons,

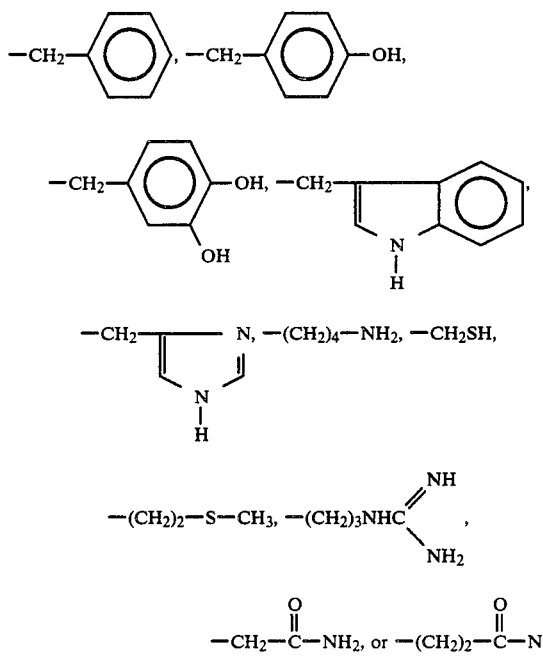

$R_6$ is hydrogen, an alkali metal salt, or

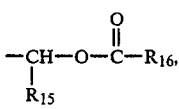

$R_{15}$ is hydrogen, methyl or isopropyl and $R_{16}$ is straight or branched chain lower alkyl of 1 to 4 carbons or phenyl.

$R_4$ is hydrogen.
$R_4$ is hydroxy.
$R_4$ is chloro or fluoro.
$R_4$ is lower alkyl of 1 to 4 carbons or cyclohexyl.
$R_4$ is amino.
$R_4$ is —O-lower alkyl wherein lower alkyl is straight or branched chain of 1 to 4 carbons.
$R_4$ is

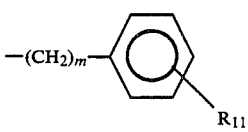

wherein m is zero, one or two, $R_{11}$ is hydrogen, methyl, methoxy, methylthio, chloro, bromo, fluoro, or hydroxy.

$R_4$ is

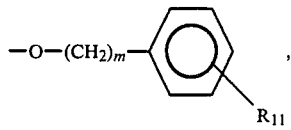

1-naphthyloxy, or 2-naphthyloxy wherein m is zero, one or two, and $R_{11}$ is hydrogen, methyl, methoxy, methylthio, chloro, bromo, fluoro, or hydroxy.

$R_4$ is —S-lower alkyl wherein lower alkyl is straight or branched chain of 1 to 4 carbons.

$R_4$ is

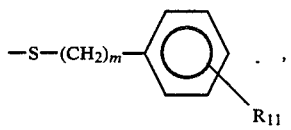

1-naphthylthio, or 2-naphthylthio wherein m is zero, one or two, and $R_{11}$ is hydrogen, methyl, methoxy, methylthio, chloro, bromo, fluoro, or hydroxy.

$R_5$ is —O-lower alkyl wherein lower alkyl is straight or branched chain of 1 to 4 carbons.

$R_5$ is

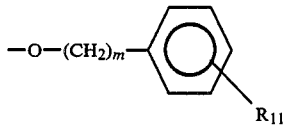

wherein m is zero, one or two, and $R_{11}$ is hydrogen, methyl, methoxy, methylthio, chloro, bromo, fluoro, or hydroxy.

$R_5$ is —S-lower alkyl wherein lower alkyl is straight or branched chain of 1 to 4 carbons.

$R_5$ is

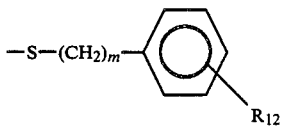

wherein m is zero, one or two, and $R_{12}$ is hydrogen, methyl, methoxy, methylthio, chloro, bromo, fluoro or hydroxy.

$R_7$ is phenyl, 2-hydroxyphenyl, or 4-hydroxyphenyl.

Each $R_8$ is independently fluoro or chloro.

Each $R_8$ is independently —Y-$R_{14}$ wherein Y is O or S, $R_{14}$ is straight or branched chain alkyl of 1 to 4 carbons or the $R_{14}$ groups join to complete an unsubstituted 5- or 6-membered ring or said ring in which one or more of the carbons has a methyl or dimethyl substituent.

$R_9$, $R'_9$, $R_{10}$ and $R'_{10}$ are all hydrogen, or $R_9$ is phenyl, 2-hydroxyphenyl or 4-hydroxyphenyl and $R'_9$, $R_{10}$ and $R'_{10}$ are hydrogen.

Most preferred compounds of this invention with respect to the amino or imino acid or ester part of the structure of formula I are those wherein:

X is

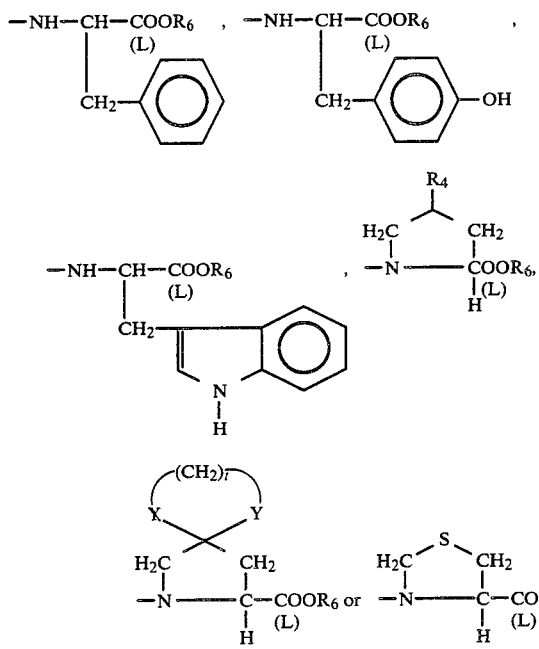

$R_6$ is hydrogen,

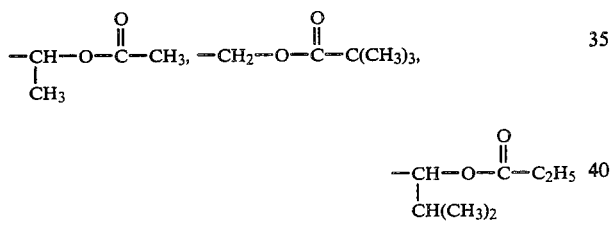

or an alkali metal salt.

$R_4$ is hydrogen.
$R_4$ is cyclohexyl.
$R_4$ is lower alkoxy of 1 to 4 carbons.
$R_4$ is

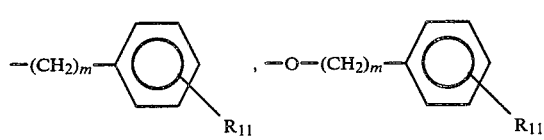

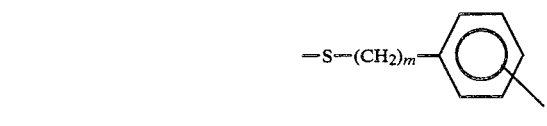

wherein m is zero, one, or two and $R_{11}$ is hydrogen, methyl, methoxy, methylthio, Cl, Br, F or hydroxy.

Y is oxygen or sulfur and t is two or three, especially wherein Y is sulfur and t is two.

Preferred compounds of this invention with respect to the phosphonyl sidechain of the structure of formula I are those wherein:

$R_2$ is hydrogen, lower alkyl of 1 to 4 carbon, $CF_3$, or amino substituted lower alkyl of 1 to 4 carbons, especially hydrogen, methyl or $-(CH_2)_4NH_2$.

$R_3$ is hydrogen, an alkali metal salt, lower alkyl of 1 to 4 carbons, or

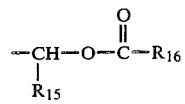

wherein $R_{15}$ is hydrogen, methyl or isopropyl and $R_{16}$ is straight or branched chain lower alkyl of 1 to 4 carbons or phenyl, especially hydrogen, alkali metal salt, ethyl,

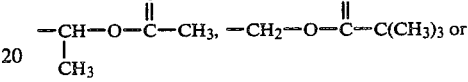

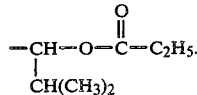

$R_1$ is alkyl of 1 to 10 carbons;

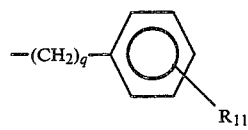

wherein q is zero or an integer from 1 to 4 and $R_{11}$ is hydrogen, methyl, methoxy, methylthio, chloro, bromo, fluoro, or hydroxy; $-(CH_2)_q-$ cycloalkyl wherein cycloalkyl is of 5 or 6 carbons and q is zero, one or two;

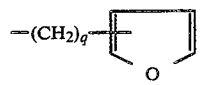

wherein q is zero or an integer from 1 to 4,

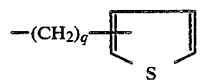

wherein q is zero or an integer from 1 to 4,

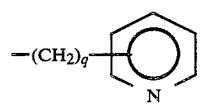

wherein q is zero or an integer from 1 to 4 or

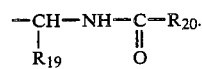

$R_{19}$ and $R_{20}$ are independently selected from lower alkyl of 1 to 4 carbons or

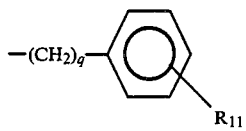

wherein q is zero or an integer from 1 to 4 and $R_{11}$ is hydrogen, methyl, methoxy, methylthio, chloro, bromo, fluoro, or hydroxy, especially wherein $R_{19}$ is phenylethyl and $R_{20}$ is phenyl.

The compounds of this invention wherein at least one of $R_3$ or $R_6$ is hydrogen, form basic salts with various inorganic and organic bases which are also within the scope of the invention. Such salts include ammonium salts, alkali metal salts like lithium, sodium and potassium salts (which are preferred), alkaline earth metal salts like calcium and magnesium salts, salts with organic bases, e.g., dicyclohexylamine salt, benzathine, N-methyl-D-glucamine, hydrabamine salts, salts with amino acids like arginine, lysine and the like. The nontoxic physiologically acceptable salts are preferred, although other salts are also useful, e.g., in isolating or purifying the product. The salts are formed using conventional techniques.

As shown above, the amino or imino acid or ester portion of the molecule of the products of formula I represented by X is in the L-configuration. Depending upon the definition of $R_2$ and $R_{19}$ other asymmetric center may be present in the phosphonyl sidechain. Thus, some of the compounds can accordingly exist in diastereoisomeric forms or in mixtures thereof. The above described processes can utilize racemates, enantiomers or diastereomers as starting materials. When diastereomeric products are prepared, they can be separated by conventional chromatographic or fractional crystallization methods.

The products of formula I wherein the imino acid ring is monosubstituted give rise to cis-trans isomerism. The configuration of the final product will depend upon the configuration of the $R_4$, $R_5$ and $R_7$ substituent in the starting material.

The compounds of formula I, and the physiologically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood pressure, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→agiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two to four divided daily doses, provided on a basis of about 0.1 to 100 mg per kilogram of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg of a compound of this invention, and about 15 to 300 mg, preferably about 15 to 200 mg of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichloromethiazide, polythiazide or benzthiazide as well as ethacrynic acid, tricynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg of a compound of formula I is compounded with physiologically acceptable vehicle, carrier, excipient, binder, preservatives, stabilizer, flavor, etc., in a unit dosage form as called for by accepted pharmaceutical practice. The amount of active substance in these compositions or preparations is such that a suitable dosage in the range indicated is obtained.

The following examples are illustrative and present preferred embodiments of the invention. Temperatures are given in degrees centigrade. AG-50W-X8 refers to a crosslinked polystyrenedivinylbenzene sulfonic acid cation exchange resin. HP-20 refers to a porous crosslinked polystyrene-divinyl benzene polymer resin.

EXAMPLE 1

(±)-1-[2-[[Hydroxy(4-phenylbutyl)phosphinyl]oxy]-1-oxopropyl]-L-proline, dilithium salt

A. (4-Phenylbutyl)phosphonic acid

A mixture of 4-phenylbutyl chloride (8.0 g, 47.5 mmole) and triethylphosphite (15.0 ml, 72 mmole) was heated at reflux (bath temperature 185° C.) under argon for 41.5 hours. Distillation of the mixture gave pure diethyl (4-phenylbutyl)phosphonate (10.8 g, 84%) as a colorless liquid, b.p. 152°-154° C. (1.0 mmHg). TLC (EtOAc) single spot $R_f$=0.55.

A mixture of diethyl (4-phenylbutyl)phosphonate (3.5 g, 13.0 mmole) and 6N HCl (45 ml) was refluxed under argon for 16 hours. The cooled reaction mixture was extracted with EtOAc. The organic phase was washed with saturated NaCl, dried (MgSO$_4$), and evaporated. The crude product (2.3 g) was recrystallized from diisopropyl ether to give pure (4-phenylbutyl)phosphonic acid (1.7 g, 61%) as white needles, m.p. 92°-93° C.

Analysis Calcd for $C_{10}H_{15}O_3P$: C, 56.07; H, 7.06; P, 14.46 Found: C, 55.83; H, 7.04; P. 14.34.

B. (±)-2-[[Phenylmethoxy(4-phenylbutyl)phosphinyl]oxy]propionic acid, ethyl ester A mixture of 4-phenylbutyl phosphonic acid from Part A (0.70 g, 3.27 mmole), benzene (10 ml), and PCl$_5$ (1.36 g, 6.54 mmole) was refluxed under argon for 30 minutes. The benzene and POCl₃ were removed in vacuo and the residue taken up in CH₂Cl₂ (5 ml). After cooling to 0° C. (ice-bath), triethylamine (1.3 ml, 9.39 mmole) was added followed by dropwise treatment with d,l ethyl llactate (0.39 ml, 3.3 mmole) in CH₂Cl₂ (3 ml) over a 5 minute period. After 1 hour benzyl alcohol (0.35 ml, 3.3 mmole) in CH₂Cl₂ (3 ml) was added dropwise over 2 minutes, the ice-bath removed, and the reaction mixture allowed to stir for 2 hours. The reaction mixture was diluted with EtOAc then washed with H₂O, 5% KHSO₄, saturated NaHCO₃, brine, dried (MgSO₄), and evaporated. The residue (1.3 g) was chromatographed on silica (70 g) eluting with 2/1 hexane/EtOAc to obtain the title compound (0.80 g, 1.98 mmole; 60% yield) as an oil.

TLC (2/1 hexane/EtOAc) two isomers $R_f$=0.25, 0.20.

C.
(±)-2-[[Phenylmethoxy(4-phenylbutyl)phosphinyl]oxy]propionic acid

A mixture of the ethyl ester from Part B (0.80 g, 1.98 mmole), 1N NaOH (3.0 ml, 3.0 mmole) and dioxane (10 ml) was stirred at 25° C. in an argon atmosphere for 2 hours. The reaction mixture was diluted with H₂O and then washed with EtOAc. The aqueous phase was acidified to pH=1.0 with concentrated HCl and the resulting oil was extracted into EtOAc. The EtOAc extract was washed with brine, dried (MgSO₄), and evaporated to give the title compound (0.70 g, 1.86 mmole, 94% yield) as an oil.

TLC (1/9 CH₃OH/CH₂Cl₂) major spot $R_f$=0.5.

D.
(±)-1-[2-[[Phenylmethoxy(4-phenylbutyl)phosphinyl]oxy]-1-oxopropyl]-L-proline, phenylmethyl ester A mixture of mono acid from Part C (0.70 g, 1.86 mmole), 1,1-carbonyldiimidazole (0.30 g, 1.85 mmole) and dry THF (10 ml) was stirred at 0° C. in an argon atmosphere for 1 hour. Triethylamine (0.26 ml, 1.88 mmole) and L-proline, phenylmethyl ester, hydrochloride salt (commercially available) (0.45 g, 1.86 mmole) were added to the resulting imidazolide and the ice-bath removed. After 60 hours the reaction mixture was diluted with EtOAc, then washed with H₂O, 5% KHSO₄, saturated NaHCO₃, brine, dried (MgSO₄), and evaporated. The residue (850 mg) was chromatographed on silica (45 g) eluting with 5/2 hexane/acetone to obtain the title compound (0.40 g, 0.71 mmole, 38% yield) as an oil.

TLC (5/2 hexane/acetone) single spot $R_f$=0.2.

E.
(±)-1-[2-[[Hydroxy(4-phenylbutyl)-phosphinyl]oxy]-1-oxopropyl]-L-proline, dilithium salt A mixture of the dibenzyl ester from Part D (0.40 g, 0.71 mmole), 10% Pd/C (50 mg), and CH₃OH (40 ml) was hydrogenated on the Parr apparatus at 50 psi for 3 hours. The catalyst was removed by filtration (celite bed) and the filtrate was evaporated. The resiude was taken up in H₂O (2 ml) and 0.1M Li₂CO₃ (3.5 ml, 0.35 mmole) and passed through an AG50WX8(Li) (40 ml) column. The desired fractions were combined, filtered (millipore), and lyophilized to give the title product (245 mg, 0.62 mmole), 87% yield) as a glassy solid.

TLC (7/2/1 isopropanol/conc. NH₄OH/H₂O) single spot $R_f$=0.8.

Analysis calcd for C₁₈H₂₄NO₆P.2Li.1.0 mole H₂O: C, 52.31; H, 6.34; N, 3.39; P, 7.5. Found: C, 52.44; H, 6.14; N, 3.63; P, 7.2.

EXAMPLE 2
1-[(S)-2-[[[(±)-1-(Benzoylamino)-3-phenylpropyl]-phosphinyl]oxy]-1-oxopropyl]-L-proline, dilithium salt

A. (1-Amino-3-phenylpropyl)phosphonic acid

To a stirred solution of benzyl carbamate (15 g, 0.1 mole) and phosphorus trichloride (9 ml, 0.1 mmole) in glacial acetic acid (25 ml) at 0° (ice bath), there is added 3-phenylpropanal (20 g, 0.149 mole) dropwise over a period of 30 minutes. The resulting mixture is stirred at 0° for 5 minutes and then allowed to warm to room temperature. The mixture is then refluxed for 30 minutes, treated with 4N hydrochloric acid (125 ml) and again refluxed for one hour. After cooling, the aqueous solution is decanted from the dark organic layer, washed with ethyl acetate, and evaporated to dryness. the residue is taken up in water (50 ml) and again evaporated to dryness. This is repeated two more times. Finally, the solid residue is triturated with acetonitrile-water and dried in vacuo over phosphorus pentoxide to give 10.05 g of (1-amino-3-phenylpropyl)phosphonic acid as a white crystaline solid; m.p. 274°-278° (dec.).

B. 3-Phenyl-1-[(benzoylamino)propyl]phosphonic acid

A mixture of amino phosphonic acid prepared in Part A (3.2 g, 14.9 mmole), dioxane (20 ml), H₂O (8.0 ml), and triethylamine (7.5 ml, 54.2 mmole) at 0° C. (ice bath) was treated dropwise with benzoyl chloride (2.8 ml, 19.4 mmole) in dioxane (4.0 ml) over a 5 minute period. The ice bath was removed and the reaction mixture stirred for 2 hours, diluted with H₂O, and then washed with Et₂O. The aqueous phase was acidified to pH 1.0 with concentrated HCl and the resulting oil was extracted into EtOAc (3×), washed with brine, dried (MgSO₄), and evaporated. The residue was stirred under Et₂O/hexane to give a gummy solid, from which upon trituration with IPE (2×) the title compound (4.0 g, 12.5 mmole, 84% yield) was obtained as a white crystalline solid, m.p. 166°-168° C. TLC (7:2:1, Isopropanol/conc. NH₄OH/H₂O) major spot, $R_f$=0.4.

Analysis Calcd for C₁₀H₁₃NO₄P: N, 4.39; C. 60.10; H, 5.68; P, 9.7. Found: N, 4.34; C, 60.30; H, 5.83; P, 9.6.

C. 1-[(S)-2-Hydroxy-1-oxopropyl]-L-proline, phenylmethyl ester

A mixture of sodium lactate (1.7 g, 15.0 mmole), diphenyl phosphorylazide (3.6 ml, 16.5 mmole) and dry DMF (30 ml) at 0° C. (ice bath) in an argon atmosphere was treated with triethyl amine (2.1 ml, 15.2 mmole) and L-proline, phenylmethyl ester, hydrochloride salt (3.6 g, 15.0 mmole). After 24 hours, the reaction mixture was partitioned between EtOAc and H₂O. The aqueous phase was back extracted, the organic extracts combined, washed with 5% KHSO₄, brine, and evaporated. The residue (5.0 g) was chromatographed on silica (130 g) eluting with EtOAc/Hexane (1:1) to give the title compound (2.5 g, 9.0 mmole, 60% yield) as a white crystalline solid after evaporation, m.p. 86°-88° C.

Analysis Calcd for C₁₅H₁₉NO₄: N, 5.05; C, 64.97; H, 6.91. Found: N, 5.02; C, 64.70; H, 6.85.

D. 1-[(S)-2-[[[(±)-1-(Benzoylamino)-3-phenylpropyl]hydroxyphosphinyl]oxy]-1-oxopropyl-L-proline], phenylmethyl ester A mixture of the phosphonic acid from Part B (0.60 g, 1.9 mmole), lactoyl proline, phenylmethyl ester (from Part C) (0.52 g, 1.9 mmole), and dry THF (5 ml) at 0° C. under argon was treated with dicyclohexylcarbodiimide (0.39 g, 1.9 mmole). After 15 minutes, the reaction mixture was diluted with EtOAc and filtered to remove the dicyclohexylurea. The filtrate was washed with 5% $KHSO_4$, brine, dried ($MgSO_4$), and evaporated. The residue (1.2 g) was chromatographed on silica (60 g) eluting with (20:1:1, $CH_2Cl_2/CH_3OH/HOAc$). The desired fractions were combined and evaporated to dryness to give the title compound (1.0 g, 1.7 mmole, 90% yield) as a foam. TLC: (20:1:1, $CH_2Cl_2/CH_3OH/HOAc$) two isomers $R_f=0.15, 0.20$.

E. 1-[(S)-2-[[[(±)-1-(Benzylamino)-3-phenylpropyl]phosphinyl]oxy]-1-oxopropyl]-L-proline, dilithium salt A mixture of the phosphonic monoester from Part D (1.0 g, 1.7 mmole), 10% Pd/C (400 mg), and $CH_3OH$ (50 ml) was hydrogenated on the Parr apparatus at 50 psi for 1.5 hours. The catalyst was removed by filtration (Celite bed) and the solvent evaporated. The residue was taken up in 1N LiOH (2.5 ml, 2.5 mmole) and applied to an AG50W×8 (Li) (50 ml) column eluting with $H_2O$. The desired fractions were combined, evaporated to small volume, and chromatographed on an HP-20 (200 ml) column eluting with a linear gradient $H_2O/CH_3CN$ (0→90% $CH_3CN$). The desired fractions were combined, evaporated to dryness, taken up in $H_2O$, filtered (millipore), and lyophilized to give the title product (0.51 g, 1.0 mmole, 60% yield) as a white solid. TLC: (7:2:1, Isopropanol/conc. $NH_4OH/H_2O$) single spot $R_f=0.7$, m.p. 248°–255° C.

Analysis Calcd for $C_{24}H_{27}N_2O_7PLi_2.0.74$ moles of $H_2O$. Calcd: N, 5.45; C, 56.12; H, 5.59; P, 6.0. Found: N, 5.35; C, 56.12; H, 5.66; P, 6.0.

EXAMPLES 3-105

Following the procedure of Example 1 but employing the phosphonic acid shown in Col. I, the lactate shown in Column II, the imino acid or amino acid or ester in Col. III, and the alcohol $R_3OH$, one obtains the diester shown in Col. IV. Both the $R_3$ and $R_6$ ester groups may be removed to yield the corresponding diacid or salt as set forth in Example 1E or only the carboxylic ester group $R_6$ may be removed or in the case of Examples 77-87 only the $R_3$ ester group may be removed.

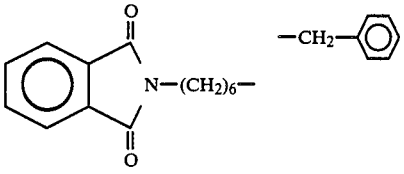

4,616,005

-continued

| Ex. | R₁ | R₃ | R₂ | X |
|---|---|---|---|---|
| 8. | O-⌬-(CH₂)₃— | —CH₂-⌬ | —CH₃ | piperidine-N, COOCH₂-⌬ (L) |
| 9. | H₃C-⌬— | —CH₂-⌬ | —(CH₂)₂-⌬ | pyrrolidine-N, COOCH₂-⌬ (L) |
| 10. | H₃CO-⌬-CH₂— | —CH₂-⌬ | —(CH₂)₄NHCOCH₂-⌬ (O) | pyrrolidine-N, COOCH₂-⌬ (L) |
| 11. | F-⌬-(CH₂)₂— | —CH₂-⌬ | —CF₃ | pyrrolidine-N, COOCH₂-⌬ (L) |
| 12. | 2-Cl-⌬-(CH₂)₄— | —CH₂-⌬ | —CH₃ | pyrrolidine-N, COOCH₂-⌬ (L) |
| 13. | H₃CS-⌬-CH₂— | —CH(-⌬)₂ | —H | pyrrolidine-N, COOC(CH₃)₃ (L) |
| 14. | cyclohexyl-(CH₂)₄— | —CH₂-⌬ | —CH₃ | pyrrolidine-N, COOCH₂-⌬ (L) |
| 15. | cyclopentyl-CH₂— | —CH₂-⌬ | —CH₃ | pyrrolidine-N, COOCH₂-⌬ (L) |
| 16. | 2-thienyl-CH₂— | —CH(-⌬)₂ | —CH₃ | pyrrolidine-N, COOC(CH₃)₃ (L) |
| 17. | 2-thienyl— | —CH(-⌬)₂ | —CH₃ | pyrrolidine-N, COOC(CH₃)₃ (L) |
| 18. | 2-furyl-CH₂— | —CH₂-⌬ | —CF₃ | pyrrolidine-N, COOCH₂-⌬ (L) |

-continued

| Ex. | R₁ | R₃ | R₂ | X |
|---|---|---|---|---|
| 19. | (furan-3-yl)-CH₂— | —CH₂—C₆H₅ | —CH₃ | pyrrolidine-2-COOC(CH₃)₃ (L) |
| 20. | (pyridin-4-yl)-CH₂— | —CH₂—C₆H₅ | —CH₃ | pyrrolidine-2-COOCH₂—C₆H₅ (L) |
| 21. | (pyridin-3-yl)-CH₂— | —CH₂—C₆H₅ | —CH₃ | pyrrolidine-2-COOCH₂—C₆H₅ (L) |
| 22. | H₃C—(CH₂)₆— | —CH₂—C₆H₅ | —CH₃ | 4-OH-pyrrolidine-2-COOCH₂—C₆H₅ (L) |
| 23. | H₃C—(CH₂)₃— | —CH₂—C₆H₅ | —CH₃ | 4-OCH₃-pyrrolidine-2-COOCH₂—C₆H₅ (L) |
| 24. | C₆H₅— | —CH(—C₆H₅)₂ | —CH₃ | 4-SCH₃-pyrrolidine-2-COOC(CH₃)₃ (L) |
| 25. | C₆H₅—CH₂— | —CH₂—C₆H₅ | —H | 4-Cl-pyrrolidine-2-COOCH₂—C₆H₅ (L) |
| 26. | C₆H₅—(CH₂)₂— | —CH₂—C₆H₅ | —CH₃ | 4-F-pyrrolidine-2-COOCH₂—C₆H₅ (L) |
| 27. | C₆H₅—(CH₂)₄— | —CH₂—C₆H₅ | —CH₃ | 4-CH₃-pyrrolidine-2-COOCH₂—C₆H₅ (L) |
| 28. | C₆H₅—(CH₂)₆— | —CH₂—C₆H₅ | —CH₃ | 4-oxo-pyrrolidine-2-COOCH₂—C₆H₅ (L) |

-continued
| Ex. | R₁ | R₃ | R₂ | X |
|---|---|---|---|---|
| 29. | 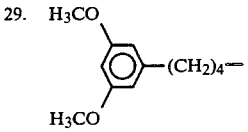 | 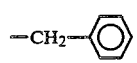 | —CH₃ | 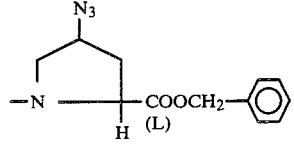 |
| 30. | 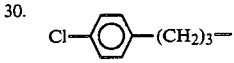 | 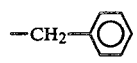 | —CH₃ | 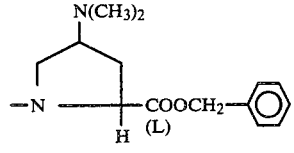 |
| 31. | 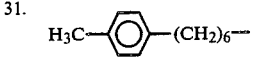 | 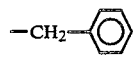 | —CH₃ | 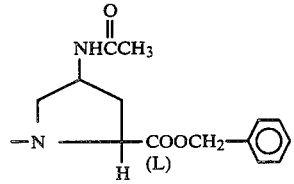 |
| 32. | 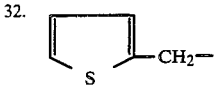 | 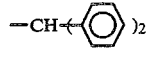 | —CH₃ | 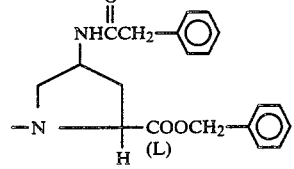 |
| 33. | 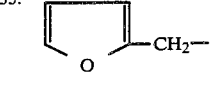 | 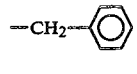 | —CH₃ | 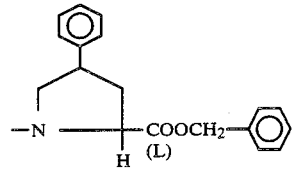 |
| 34. | 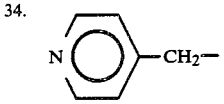 | 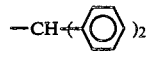 | —CH₃ | 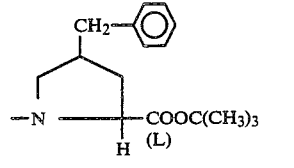 |
| 35. | 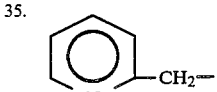 | 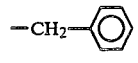 | —CH₃ | 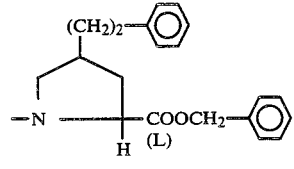 |
| 36. | H₃C— | 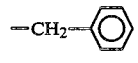 | —CH₃ | 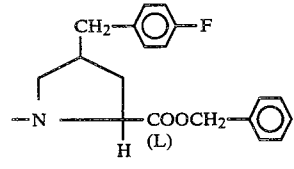 |

| Ex. | R₁ | R₃ | R₂ | X |
|---|---|---|---|---|
| 37. | H₅C₂— | —CH(Ph)₂ | —CH₃ | 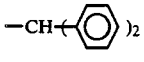 |
| 38. | Ph(CH₂)₂— | —CH₂Ph | —CH₃ | 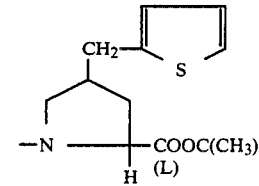 |
| 39. | thiophene-CH₂— | —CH(Ph)₂ | —CH₃ | 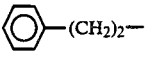 |
| 40. | furan-CH₂— | —CH₂Ph | —CH₃ | 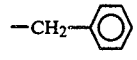 |
| 41. | pyridine-4-CH₂— | —CH₂Ph | —CH₃ | 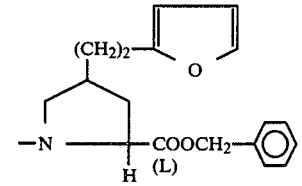 |
| 42. | H₃C—(CH₂)₅— | —CH₂Ph | —H |  |
| 43. | Ph(CH₂)₄— | —CH₂Ph | —CH₃ | 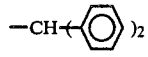 |
| 44. | Ph— | —CH₂Ph | —(CH₂)₄NHCOCH₂Ph | 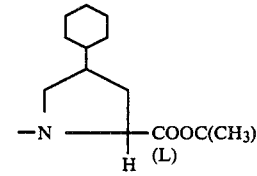 |

-continued

| Ex. | R₁ | R₃ | R₂ | X |
|---|---|---|---|---|
| 45. | PhCH₂— | —CH(Ph)₂ | —CH₃ | 4-(benzylthio)-pyrrolidine-2-COOC(CH₃)₃ (L) |
| 46. | Ph(CH₂)₂— | —CH(Ph)₂ | —CH₃ | 4-(phenylthio)-pyrrolidine-2-COOC(CH₃)₃ (L) |
| 47. | Ph(CH₂)₄— | —CH₂Ph | —CH₃ | 4-[(4-fluorophenyl)thio]-pyrrolidine-2-COOCH₂Ph (L) |
| 48. | Ph(CH₂)₄— | —CH(Ph)₂ | —CH₃ | 4-(naphthalen-2-ylthio)-pyrrolidine-2-COOC(CH₃)₃ (L) |
| 49. | H₃C—(CH₂)₃— | —CH(Ph)₂ | —CH₃ | 4-(biphenyl-4-ylthio)-pyrrolidine-2-COOC(CH₃)₃ (L) |
| 50. | H₃CO—C₆H₄—(CH₂)₄— | —CH₂Ph | —CH₃ | 4-(naphthalen-2-yloxy)-pyrrolidine-2-COOCH₂Ph (L) |
| 51. | Ph(CH₂)₂— | —CH₂Ph | —CH₃ | 4-chloro-pyrrolidine-2-COOCH₂Ph (L) |
| 52. | Ph— | —CH₂Ph | —CH₃ | 4-[OC(=O)N(CH₃)₂]-pyrrolidine-2-COOCH₂Ph (L) |
| 53. | Ph(CH₂)₄— | —CH₂Ph | —CH₃ | 4-phenoxy-pyrrolidine-2-COOCH₂Ph (L) |

-continued

| Ex. | R₁ | R₃ | R₂ | X |
|---|---|---|---|---|
| 54. | phenyl-(CH₂)₃— | —CH(phenyl)₂ | —CH₃ | N-CH₂-CH₂-CH(S-phenyl)-CH(COOCH(phenyl)₂)(L)-H |
| 55. | phenyl-(CH₂)₅— | —CH(phenyl)₂ | —CH₃ | N-CH₂-CH₂-CH(S-CH₂-phenyl)-CH(COOCH(phenyl)₂)(L)-H |
| 56. | H₃C—(CH₂)₃— | —CH₂-phenyl | —CH₃ | pyrrolidinone-N-CH(COOCH₂-phenyl)(L)-H |
| 57. | phenyl-(CH₂)₄— | —CH₂-phenyl | —CH₃ | N-CH(phenyl)-CH₂-CH₂-CH(COOCH₂-phenyl)(L)-H |
| 58. | phenyl-(CH₂)₂— | —CH₂-phenyl | —CH₃ | N-CH(2-hydroxyphenyl)-CH₂-CH₂-CH(COOCH₂-phenyl)(L)-H |
| 59. | H₃C—(CH₂)₅— | —CH₂-phenyl | —CH₃ | N-CH(4-hydroxyphenyl)-CH₂-CH₂-CH(COOCH₂-phenyl)(L)-H |
| 60. | 2-thienyl-CH₂— | —CH(phenyl)₂ | —CH₃ | N-CH₂-C(F)(F)-CH₂-CH(COOCH(phenyl)₂)(L)-H |
| 61. | 2-furyl-CH₂— | —CH₂-phenyl | —CH₃ | N-CH₂-C(OCH₃)(OCH₃)-CH₂-CH(COOCH₂-phenyl)(L)-H |
| 62. | phenyl-(CH₂)₄— | —CH(phenyl)₂ | —H | N-CH₂-C(S-S)-CH₂-CH(COOCH(phenyl)₂)(L)-H (dithiolane spiro) |
| 63. | phenyl-(CH₂)₂— | —CH₂-phenyl | —CH₃ | N-CH₂-C(O-O)-CH₂-CH(COOCH₂-phenyl)(L)-H (dioxolane spiro) |

-continued

| Ex. | R₁ | R₃ | R₂ | X |
|---|---|---|---|---|
| 64. | phenyl | —CH₂—(phenyl)₂ | —CH₃ | dithiane-containing N-substituent with —COOCH(phenyl)₂ (L) |
| 65. | H₃C—(CH₂)₄— | —CH₂—phenyl | —CH₃ | methyl-dithiane N-substituent with —COOCH₂—phenyl (L) |
| 66. | H₃CS—⟨phenyl⟩—CH₂— | —CH—(phenyl)₂ | —H | bis(dimethyl)-dithiane N-substituent with —COOCH—(phenyl)₂ (L) |
| 67. | ⟨phenyl⟩—(CH₂)₂— | —CH₂—phenyl | —CH₃ | tetrahydropyridine N-substituent with —COOCH₂—phenyl (L) |
| 68. | ⟨phenyl⟩—(CH₂)₄— | —CH—(phenyl)₂ | —C₂H₅ | thiazolidine N-substituent with —COOC(CH₃)₃ (L) |
| 69. | ⟨phenyl⟩—(CH₂)₂— | —CH—(phenyl)₂ | —CH₃ | dimethyl-thiazolidine N-substituent with —COOC(CH₃)₃ (L) |
| 70. | H₃C—(CH₂)₅— | —CH—(phenyl)₂ | —CH₃ | phenyl-thiazolidine N-substituent with —COOC(CH₃)₃ (L) |
| 71. | ⟨phenyl⟩—(CH₂)₄— | —CH₂—phenyl | —CH₃ | piperidine-2-carboxylate —COOCH₂—phenyl |
| 72. | ⟨phenyl⟩—(CH₂)₂— | —CH₂—phenyl | —CH₃ | tetrahydroquinoline N-substituent with —COOCH₂—phenyl |

-continued

| Ex. | R₁ | R₃ | R₂ | X |
|---|---|---|---|---|
| 73. | phenyl | —CH₂—phenyl | —CH₃ | tetrahydroisoquinoline-type: —N—CH(COOCH₂-phenyl)— fused to benzene via —CH₂— |
| 74. | phenyl—(CH₂)₂— | —CH₂—phenyl | —CH₃ | —N—CH(COOCH₂-phenyl)—CH₂—(2-phenylene)— (ring) |
| 75. | phenyl—(CH₂)₄— | —CH₂—phenyl | —CH₃ | tetrahydroisoquinoline: —N—CH(COOCH₂-phenyl)— with —CH₂-phenylene bridge |
| 76. | H₃C—(CH₂)₅— | —CH₂—phenyl | —H | tetrahydroisoquinoline ring: —N—CH(COOCH₂-phenyl) fused |
| 77. | phenyl—(CH₂)₄— | —CH₂—phenyl | —CH₃ | —N—CH(L)(H)—C(=O)—O—CH₂—C(=O)—C(CH₃)₃ (pyrrolidine) |
| 78. | phenyl—(CH₂)₂— | —CH(phenyl)₂ | —CH₃ | dithiolane: S,S-spiro, —N—CH(L)(H)—C(=O)—O—CH(CH₃)—C(=O)—CH₃ |
| 79. | H₃C—(CH₂)₅— | —CH₂—phenyl | —CH₃ | —N—CH(L)(H)—C(=O)—O—CH₂—C(=O)—phenyl (pyrrolidine) |
| 80. | phenyl—(CH₂)₂— | —CH(phenyl)₂ | —CH₃ | —S-phenyl substituent; —N—CH(L)(H)—C(=O)—O—CH₂—C(=O)—C(CH₃)₃ |
| 81. | thiophen-2-yl—CH₂— | —CH(phenyl)₂ | —CH₃ | naphthyloxy substituent; —N—CH(H)—C(=O)—O—CH(CH₃)—C(=O)—C₂H₅ |

-continued
| Ex. | R₁ | R₃ | R₂ | X |
|---|---|---|---|---|
| 82. | 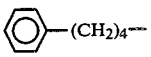 | 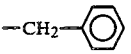 | —CH₃ | 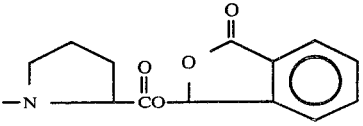 |
| 83. | 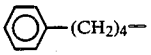 | 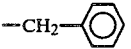 | —CH₃ | 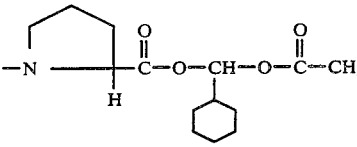 |
| 84. | 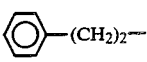 | 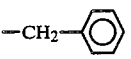 | —CH₃ | 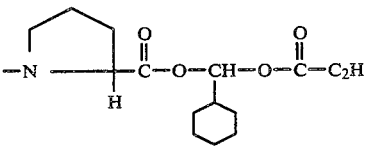 |
| 85. | 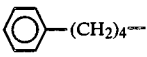 | 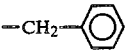 | —CH₃ | 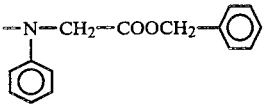 |
| 86. | 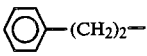 | 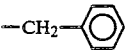 | —CH₃ | 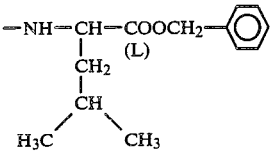 |
| 87. |  | 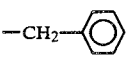 | —CH₃ | 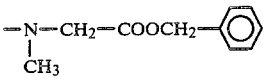 |
| 88. | 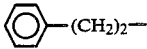 | 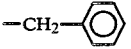 | —CH₃ | 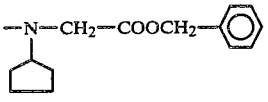 |
| 89. | 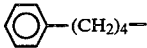 | 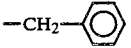 | —CH₃ | 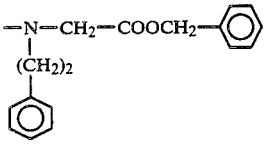 |
| 90. | H₃C—(CH₂)₅— | 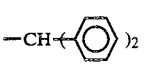 | —H | 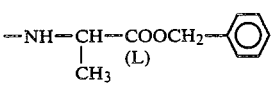 |
| 91. | 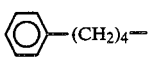 | 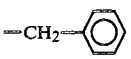 | —CH₃ | 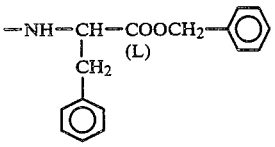 |

-continued

| Ex. | R₁ | R₃ | R₂ | X |
|---|---|---|---|---|
| 92. | Ph−(CH₂)₂− | −CH₂−Ph | −CH₃ | −NH−CH(−COOCH₂Ph)−CH₂−C₆H₄−OCH₂Ph (L) |
| 93. | Ph− | −CH(−Ph)₂ | −CH₃ | −N(Ph)−CH₂−COOCH₂Ph |
| 94. | H₅C₂− | −CH₂−Ph | −CH₃ | −NH−CH(−COOCH₂Ph)−CH₂-(indol-3-yl) (L) |
| 95. | cyclohexyl− | −CH₂−Ph | −CH₃ | −NH−CH(−COOCH₂Ph)−CH₂-(1-benzylimidazol-4-yl) (L) |
| 96. | cyclopentyl-CH₂− | −CH₂−Ph | −CH₃ | −NH−CH(−COOCH₂Ph)−(CH₂)₄−NHCOCH₂Ph (L) |
| 97. | (thien-2-yl)-CH₂− | −CH(−Ph)₂ | −CH₃ | −NH−CH(−COOCH₂Ph)−CH₂−SCH₂Ph (L) |
| 98. | (furan-2-yl)-CH₂− | −CH₂−Ph | −CH₃ | −NH−CH(−COOCH₂Ph)−(CH₂)₂−S−CH₃ (L) |
| 99. | Ph−(CH₂)₂− | −CH₂−Ph | −CH₃ | −NH−CH(−COOCH₂Ph)−(CH₂)₃−NHC(=NH)−NH−NO₂ (L) |
| 100. | Ph−(CH₂)₄− | −CH(−Ph)₂ | −CH₃ | −NH−CH(−COOCH₂Ph)−CH₂−C(=O)NH₂ |
| 101. | H₃C−(CH₂)₅− | −CH₂−Ph | −CH₃ | −N(cyclohexyl)−CH₂−COOCH₂Ph |

-continued

| Ex. | R₁ | R₃ | R₂ | X |
|-----|----|----|----|---|
| 102. | C₆H₅—(CH₂)₂— | —CH₂—C₆H₅ | H | —NH—CH(CH₃)—COOCH₂—C₆H₅ (L) |
| 103. | H₃C—(CH₂)₅— | —CH₂—C₆H₅ | CH₃ | —NH—CH(CH₂—C₆H₄—OCH₂—C₆H₅)—COOCH₂—C₆H₅ (L) |
| 104. | H₃C—CH₂— | —CH₂—C₆H₅ | C₂H₅ | —NH—CH₂—COOCH₂—C₆H₅ |
| 105. | C₆H₅—(CH₂)₄— | —CH₂—C₆H₅ | H | —NH—CH(CH₂—C₆H₅)—COOCH₂—C₆H₅ (L) |

EXAMPLES 106 TO 124

Following the procedure of Example 2 but employing the phosphonic acid shown in Col. I, the acid chloride shown in Col. II, and the hydroxyacyl imino ester shown in Col. III, one obtains the intermediate shown in Col. IV. Removal of the carboxylic acid protecting group yields the compound of Col. V which can be treated to obtain a salt as shown in Example 2, Part E.

| Col. I | Col. II | Col. III |
|--------|---------|----------|
| H₂N—CH(R₁₉)—P(O)(OH)—OH | R₂₀—C(O)—Cl | HO—CH(R₂)—C(O)—X |

| Col. IV | Col. V |
|---------|--------|
| R₂₀—C(O)—NH—CH(R₁₉)—P(O)(OH)—O—CH(R₂)—C(O)—X | R₂₀—C(O)—NH—CH(R₁₉)—P(O)(OH)—O—CH(R₂)—C(O)—X |

| Ex. | R₁₉ | R₂ | X | R₂₀ |
|-----|-----|----|----|-----|
| 106. | —(CH₂)₂—C₆H₅ | —CH₃ | —N(pyrrolidine, L)—COOCH₂—C₆H₅ | —C₆H₅—CH₂— |
| 107. | —(CH₂)₂—C₆H₅ | —CH₃ | —N(pyrrolidine, L)—COOCH₂—C₆H₅ | —C₆H₅—(CH₂)₂— |
| 108. | —(CH₂)₂—C₆H₅ | —CH₃ | —N(pyrrolidine, L)—COOCH₂—C₆H₅ | H₃C— |
| 109. | —CH₂—C₆H₅ | —CH₃ | —N(pyrrolidine, L)—COOCH₂—C₆H₅ | tetrahydrofuran-2-yl |

-continued

| Ex. | R₁₉ | R₂ | X | R₂₀ |
|---|---|---|---|---|
| 110. | —(CH₂)₂—C₆H₅ | —CH₃ | —N—CH(L)(H)—(CH₂)₃—COOCH₂—C₆H₄— | H₃C—C₆H₄— |
| 111. | —C₆H₅ | —CH₃ | —N—CH(L)(H)—(CH₂)₃—COOCH₂—C₆H₄— | F₃C— |
| 112. | —(CH₂)₂—C₆H₅ | —CH₃ | —N—CH(L)(H)—(CH₂)₃—COOCH₂—C₆H₄— | H— |
| 113. | —CH₃ | —CH₃ | —N—CH(L)(H)—(CH₂)₃—COOCH₂—C₆H₄— | C₆H₅— |
| 114. | —(CH₂)₂—C₆H₅ | —CH₃ | —N—CH(L)(H)—(CH₂)₃—COOCH₂—C₆H₄— | cyclohexyl— |
| 115. | —CH₂-(2-thienyl) | —CH₃ | —N—CH(L)(H)—(CH₂)₃—COOCH₂—C₆H₄— | Cl—C₆H₄— |
| 116. | —(CH₂)₂-(2-furyl) | —CH₃ | —N—CH(L)(H)—(CH₂)₃—COOCH₂—C₆H₄— | C₆H₅—CH₂—O—C₆H₄—CH₂— |
| 117. | —(CH₂)₂—C₆H₅ | —CH₃ | —N—CH(L)(H)—(CH₂)₃—COOCH₂—C₆H₄— | (pyridyl)—CH₂— |
| 118. | —H | —CH₃ | —N—CH(L)(H)—(CH₂)₃—COOCH₂—C₆H₄— | (2-thienyl)— |
| 119. | —(CH₂)₂—C₆H₅ | —(CH₂)₄NHCOCH₂—C₆H₅ | —N—CH(L)(H)—(CH₂)₃—COOCH₂—C₆H₄— | C₆H₅— |

-continued

| Ex. | R₁₉ | R₂ | X | R₂₀ |
|---|---|---|---|---|
| 120. | —(CH₂)₂—C₆H₅ | —CH₃ | [proline with S,S dithioketal, —N—COOCH₂—C₆H₅, H(L)] | —C₆H₅ |
| 121. | —(CH₂)₂—C₆H₅ | —H | [L-proline, —N—COOCH₂—C₆H₅, H(L)] | tetrahydrofuran-2-yl-CH₂— |
| 122. | —(CH₂)₂—C₆H₅ | —H | [L-proline, —N—COOCH₂—C₆H₅, H(L)] | —C₆H₅ |
| 123. | —(CH₂)₂—C₆H₅ | —C₂H₅ | [tetrahydroisoquinoline, —N—COOCH₂—C₆H₅, H] | —C₆H₅ |
| 124. | —(CH₂)₂—C₆H₅ | —CH₃ | —NH—CH₂—COOCH₂—C₆H₅ | —C₆H₅ |

EXAMPLE 125

(±)-1-[2-[[[(2,2-Dimethyl-1-oxopropoxy)methoxy](4-phenylbutyl)phosphinyl]oxy]-1-oxopropyl]-L-proline

A.

(±)-1-[2-[[Phenylmethoxy(4-phenylbutyl)-phosphinyl]oxy]-1-oxopropyl]-L-proline, 1,1-dimethylethyl ester Following the procedure of Example 1, Part D, using L-proline, 1,1-dimethylethyl ester in place of L-proline, phenylmethyl ester gives the title compound.

B.

(±)-1-[2-[[Hydroxy(4-phenylbutyl)phosphinyl]oxy]-1-oxopropyl]-L-proline, 1,1-dimethylethyl ester A mixture of the benzyl ester from Part A (1.03 g, 2.0 mmole) 10% Pd/C (0.20 g) and methanol (50 ml) is hydrogenated on a Parr apparatus at a pressure of 50 psi for 3 hours. The catalyst is removed by filtration through celite and the filtrate evaporated to dryness to give the title compound.

C.

(±)-1-[2-[[[(2,2-Dimethyl-1-oxopropyl)methoxy](4-phenylbutyl)phosphinyl]oxy]-1-oxopropyl]-L-proline, 1,1-dimethylethyl ester A solution of the monoacid from Part B (0.64 g, 1.5 mmole), triethylamine (0.42 ml, 3.0 mmole) and chloromethyl pivalate (0.45 g, 3.0 mmole) in dry dimethylformamide (5 ml) is stirred at room temperature under argon for 16 hours. The mixture is then partitioned between EtOAc-water. The organic phase is washed successively with 5% KHSO₄, saturated NaHCO₃ and saturated NaCl, dried over Na₂SO₄ and evaporated. The crude product is purified by flash chromatography on silica gel to give the title compound.

D.

(±)-1-[2-[[[(2,2-Dimethyl-1-oxopropoxy)methoxy](4-phenylbutyl)phosphinyl]oxy]-1-oxopropyl]-L-proline A solution of the diester from Part C (0.54 g, 1.0 mmole) and anisole (2 ml) in CH₂Cl₂ (10 ml) is treated with trifluoroacetic acid (5 ml) at 0° C. (ice bath). After 1 hour at 0° C., the mixture is partitioned between EtOAc-water. The organic phase is washed with water and saturated NaCl, dried over Na₂SO₄ and evaporated. The crude product is purified by flash chromatography on silica gel to give the title compound.

EXAMPLES 126–130

Following the procedure of Example 125 but employing the alkylating agent shown in Col. I in place of the chloromethyl pivalate, one obtains the product in Col. II.

| Ex. | Col. I | Col. II |
|---|---|---|
| 126. | BrCH₂OC(=O)—CH₃ | (±)-1-[2-[[[(Acetyloxy)methoxy](4-phenylbutyl)phosphinyl]oxy]-1-oxopropyl]-L-proline |
| 127. | Cl—CH(CH₃)—O—COC₂H₅ (=O) | (±)-1-[2-[[[1-(Ethoxycarbonyl)oxy]ethoxy](4-phenylbutyl)phosphinyl]oxy]-1-oxopropyl]-L-proline |

| Ex. | Col. I | Col. II |
|---|---|---|
| 128. | Br-[structure: bromo-substituted isobenzofuranone] | (±)-1-[2-[[(3-Oxo-1-isobenzofuranyloxy)(4-phenylbutyl)phosphinyl]oxy]-1-oxopropyl]-1-L-proline |
| 129. | ClCH$_2$O—C(=O)—[phenyl] | (±)-1-[2-[[[(Benzoyloxy)methoxy](4-phenylbutyl)phosphinyl]oxy]-1-oxopropyl]-L-proline |
| 130. | Cl—CH(CH(CH$_3$)$_2$)—O—C(=O)—C$_2$H$_5$ | (±)-1-[2-[[[2-Methyl-1-(1-oxopropoxy)propoxy](4-phenylbutyl)phosphinyl]oxy]-1-oxopropyl]-L-proline |

Similarly, the alkylating agents of Examples 125–130 can be employed with the appropriately protected compounds of Examples 1 to 124 to yield other compounds within the scope of this invention. In the cases where the proline carboxyl group is protected as its phenylmethyl ester rather than its t-butyl ester, it is removed by hydrogenation in the presence of Pd/C in the final step.

EXAMPLE 131

(±)-[2-[[Hydroxy(4-phenylbutyl)phosphinyl]oxy]-1-oxopropyl]-L-proline, disodium salt Following the procedure of Example 1 but substituting AG-50W-X8 (Na$^+$) for the lithium resin in Part E, one obtains the title product.

This procedure can be employed in Examples 2–130 to give the corresponding mono or disodium salt. Similarly, by employing a potassium resin the corresponding mono or dipotassium salt is obtained.

EXAMPLE 132

1000 Tablets each containing the following ingredients:

| | |
|---|---|
| (±)-[2-[[Hydroxy(4-phenylbutyl)phosphinyl]oxy]-1-oxopropyl]-L-proline, disodium salt | 100 mg |
| Corn starch | 50 mg |
| Gelatin | 7.5 mg |
| Avicel (microcrystalline cellulose) | 25 mg |
| Magnesium stearate | 2.5 mg |
| | 185 mg | are prepared from sufficient bulk quantities by mixing the (±)-[2-[[hydroxy(4-phenylbutyl)phosphinyl]oxy]-1-oxopropyl]-L-proline, disodium salt and corn starch with an aqueous solution of the gelatin. The mixture is dried and ground to a fine powder. The Avicel and then the magnesium stearate are admixed with granulation. This mixture is then compressed in a tablet to form 1000 tablets each containing 100 mg of active ingredient.

In a similar manner, tablets containing 100 mg of the product of any of Examples 2 to 130 can be prepared.

EXAMPLE 133

1000 tablets each containing the following ingredients:

| | |
|---|---|
| 1 (S)—2-[[[(±)-1-(Benzoylamino)-3-phenylpropyl]phosphinyl]oxy]-1-oxopropyl]-L-proline, sodium salt | 50 mg |
| Lactose | 25 mg |
| Avicel | 38 mg |
| Corn starch | 15 mg |
| Magnesium stearate | 2 mg |
| | 130 mg | are prepared from sufficient bulk quantitites by mixing the 1-[(S)-2-[[[(±)-1-(benzoylamino)-3-phenylpropyl]phosphinyl]oxy]-1-oxopropyl]-L-proline, sodium salt, lactose and Avicel and then blending with the corn starch. Magnesium stearate is added and the dry mixture is compressed in a tablet press to form 1000 tablets each containing 50 mg of active ingredient. The tablets are coated with a solution of Methocel E 15 (methyl cellulose) including as a color a lake containing yellow #6.

In a similar manner, tablets containing 50 mg of the product of any of Examples 1 and 3 to 130 can be prepared.

EXAMPLE 134

Two piece #1 gelatin capsules each containing 100 mg of 1-[(S)-2-[[[(±)-1-(benzoylamino)-3-phenylpropyl]phosphinyl]oxy]-1-oxopropyl]-L-proline, sodium salt are filled with a mixture of the following ingredients:

| | |
|---|---|
| 1-[(S)—2-[[[(±)-1-(Benzoylamino)-3-phenylpropyl]phosphinyl]oxy]-1-oxopropyl]-L-proline, sodium salt | 100 mg |
| Magnesium stearate | 7 mg |
| Lactose | 193 mg |
| | 300 mg |

In a similar manner, capsules containing 100 mg of the product of any of Examples 1 and 3 to 130 can be prepared.

EXAMPLE 135

An injectable solution is prepared as follows:

| | |
|---|---|
| (±)-1-[2-[[Hydroxy(4-phenylbutyl)phosphinyl]oxy]-1-oxopropyl]-L-proline, disodium salt | 500 g |
| Methyl paraben | 5 g |
| Propyl paraben | 1 g |
| Sodium chloride | 25 g |
| Water for injection | 5 l |

The active substance, preservatives, and sodium chloride are dissolved in 3 liters of water for injection and then the volume is brought up to 5 liters. The solution is filtered through a sterile filter and asceptically filled into presterilized vials which are closed with presterilized rubber closures. Each vial contains 5 ml of solution in a concentration of 100 mg of active ingredient per ml of solution for injection.

In a similar manner, an injectable solution containing 100 mg of active ingredient per ml of solution can be prepared for the product of any of Examples 2 to 130.

EXAMPLE 136

1000 Tablets each containing the following ingredients:

| | |
|---|---|
| (±)-1-[2-[[Hydroxy(4-phenylbutyl)-phosphinyl]oxy]-1-oxopropyl]-L-proline, disodium salt | 100 mg |
| Avicel | 100 mg |
| Hydrochlorothiazide | 12.5 mg |
| Lactose | 113 mg |
| Corn starch | 17.5 mg |
| Stearic acid | 7 mg |
| | 350 mg | are prepared from sufficient bulk quantities by slugging the (±)-1-[2-[[hydroxy(4-phenylbutyl)-phosphinyl]oxy]-1-oxopropyl]-L-proline, disodium salt, Avicel and a portion of the stearic acid. The slugs are ground and passed through a #2 screen, then mixed with the hydrochlorothiazide, lactose, corn starch, and remainder of the stearic acid. The mixture is compressed into 350 mg capsule shaped tablets in a tablet press. The tablets are scored for dividing in half.

In a similar manner, tablets can be prepared containing 100 mg of the product of any of Examples 2 to 130.

EXAMPLE 137

(S)-N-[6-Amino-2-[[hydroxy(4-phenylbutyl)phosphinyl]oxy]-1-oxohexyl]-N-cyclohexylglycine, dilithium salt

A. (S)-6-Amino-2-hydroxyhexanoic acid

[Ref. Chem. Pharm. Bull. 24(4), 621–631 (1976)]

An aqueous solution of L-lysine•HCl (18.3 gm, 0.10 mole) was passed through a AG3-X4A (100–200 mesh) ion exchange column (OH$^\ominus$ form, 500 ml bed volume) eluting with water. The ninhydrin positive fractions were combined, acidified with 2M (4N) $H_2SO_4$ (100 ml, 0.2 mole) and evaporated to dryness.

The crude L-lysine•$2H_2SO_4$ was taken up in 10% $H_2SO_4$ (250 ml) and treated dropwise with a solution of sodium nitrite (25.9 gm, 0.36 mole) in water (100 ml) at 45°–50° C. (bath temperature) over a period of 2 hours. When the addition was complete, the mixture was stirred at 45°–50° C. for an additional 4.5 hours, the excess nitrous acid decomposed with urea and the mixture poured onto an AG-50-X8 ion exchange column (H$^+$ form, 200 ml bed volume). The column was eluted with water and then aqueous $NH_4OH$ (conc. $NH_4OH$-$H_2O$; 1:3) to elute the product. The ninhydrin positive fractions were combined and evaporated to give a pink semi-solid which was recrystallized from $H_2O$-EtOH to give title compound (8.20 gm, 56%) as white crystals, m.p. 197°–199° C. $[\alpha]_D = -12.2°$ (c=1.2, $H_2O$) [Lit m.p. 203°–206° C., $[\alpha]_D = -12.1°$ (c=1.16, $H_2O$)]. TLC (i-PrOH-conc. $NH_4OH$-$H_2O$; 7:2:1) $R_f=0.16$ (contains trace of lysine, $R_f=0.02$).

B. (S)-6-[[(Phenylmethoxy)carbonyl]amino]-2-hydroxyhexanoic acid

A solution of Part A aminohydroxy acid (7.50 gm, 51.0 mmole) in 1N NaOH solution (50 ml) at 0° C. (ice bath) was adjusted to pH 10 with concentrated HCl and treated with benzyl chloroformate (8.40 ml, 95%, 55.9 mmole) in ~1 ml portions at 15 minute intervals. Throughout the reaction, the pH was maintained at pH 9.8–10.2 by the addition of 1N NaOH solution. When the addition was complete and pH had stabilized, the mixture was stirred at pH 10, 0° C. for an additional 45 minutes, then washed with one portion of $Et_2O$. The aqueous solution was acidified to pH 1 with concentrated HCl and extracted with EtOAc. The EtOAc extract was washed with saturated NaCl solution, dried over $Na_2SO_4$ and evaporated. The residue was crystallized from i-$Pr_2O$ to give crude title compound (13.5 gm, 94%) as a white solid. Recrystallization of the crude product from EtOAc-hexane gave pure title compound (11.48 gm, 80%) as a white crystalline solid, m.p. 79°–81° C. $[\alpha]_D = +4.5°$, $[\alpha]_{365} = +26.8°$ (c=1.1, $CHCl_3$), [Lit. m.p. 79°–81° C., $[\alpha]_{589} = +2.7°$, $[\alpha]_{365} = +21.4°$ (c=1, $CHCl_3$)]TLC (AcOH-MeOH-$CH_2Cl_2$; 1:1:20) $R_f=0.19$.

C. (S)-6-[[(Phenylmethoxy)carbonyl]amino]-2-hydroxyhexanoic acid, methyl ester A mixture of Part B hydroxy acid (4.0 g, 14.2 mm) and $CH_3I$ (0.97 ml, 15.6 mmole, 1.1 eq) in dry DMF (15 ml) was treated with powdered $K_2CO_3$ (2.55 g, 18.5 mmole, 1.3 eq) and the light yellow suspension was stirred under argon for 2.0 hours at room temperature. The mixture was partitioned between 5% $KHSO_4$ and EtOAc, the organic phase washed with $H_2O$ (2×), saturated $NaHCO_3$ and brine, then dried over anhydrous $Na_2SO_4$ and evaporated to give 3.703 g (88%) of desired methyl ester as a viscous, pale yellow oil with consistent $C^{13}$ NMR ($CDCl_3$, 15 MHz) spectral data. TLC (9:1) EtOAc-Hex, $R_f=0.69$, UV+PMA.

D. 4-Phenylbutylphosphonous acid

To a suspension of sodium hypophosphite•$H_2O$ (60.0 gm, 0.566 mole) in absolute ethanol (600 ml) was added concentrated $H_2SO_4$ (15 ml), 4-phenyl butene (25.0 gm, 0.189 mole) and azobisisobutyronitrile (3.0 gm). The resulting mixture was refluxed for 6 hours, treated with a second portion of AIBN (2.0 gm) and refluxed for an additional 16 hours. The cooled mixture was filtered and concentrated in vacuo. The residue was suspended in water (200 ml), made basic with 50% NaOH solution and washed with two portions of $Et_2O$ (200 ml each). The aqueous phase was acidified with concentrated $H_2SO_4$ and extracted with EtOAc. The EtOAc extract was washed with saturated NaCl, dried over $Na_2SO_4$ and evaporated to give 34.5 gm (92%) of crude title phosphonous acid. TLC (i-PrOH—concentrated $NH_4OH$—$H_2O$; 7:2:1) $R_f=0.67$, trace impurity at $R_f=0.78$.

The crude title phosphonous acid was purified by conversion to its 1-adamantanamine salt. Thus, the crude title phosphonous acid (34.5 gm) was taken up in $Et_2O$ (200 ml) and treated with a solution of 1-adamantanamine (26.3 gm, 0.174 mole) in $Et_2O$ (200 ml). The white precipitate was collected, washed with $Et_2O$ and dried in vacuo to give title adamantanamine salt of the above title compound (54.2 gm, 82% from 4-phenylbutene) as a white solid, m.p. 192°–200° C.

To regenerate the free acid, the adamantanamine salt (10.5 gm) was partitioned between EtOAc—1N HCl (150 ml each). The EtOAc phase was washed with 1N HCl and saturated NaCl, dried over $Na_2SO_4$ and evaporated to give pure title acid (5.75 gm, 96%) as a colorless, viscous oil. TLC (i-PrOH—concentrated $NH_4OH$—$H_2O$; 7:2:1) single spot, $R_f=0.67$.

E. (S)-2-[[(4-Phenylbutyl)phosphinyl]oxy]-6-[[(phenylmethoxy)carbonyl]amino]hexanoic acid, methyl ester A mixture of Part C hydroxy ester (3.323 g, 11.3 mmole, 1 eq) and Part D phosphonous acid (3.37 g, 17 mmole, 1.5 eq) in dry THF (30 ml) was treated with N,N-dicyclohexylcarbodiimide (DCC) (3.51 g, 17 mm, 1.5 eq) and 4-(N,N-dimethylamino)pyridine (DMAP) (208 mg, 1.7 mm, 0.15 eq) and the white suspension stirred at room temperature under argon for 40 minutes. The mixture was diluted with EtOAc, precipitated dicyclohexylurea (DCU) filtered off, the filtrate washed with 5% $KHSO_4$, saturated $NaHCO_3$ and brine then dried over anhydrous $Na_2SO_4$ and evaporated. Baseline impurities were removed by chromatography on a $\frac{3}{4}''$ pad of Silicar CC-7 silica gel eluting with (9:1) EtOAc-Hex. Product fractions were evaporated to give 5.77 g of title compound as a viscous oil plus residual DCU. $C^{13}$ NMR was consistent for coupled product ($CDCl_3$, 15 MHz). TLC (9:1) EtOAc-Hex, $R_f = 0.23$, UV+PMA.

F. (S)-2-[[Hydroxy(4-phenylbutyl)phosphinyl]oxy]-6-[[(phenylmethoxy)carbonyl]amino]hexanoic acid, methyl ester A mixture of Part E phosphonous ester (5.77 g, crude) in dioxane (60 ml) was treated with an aqueous $NaIO_4$ solution (2.78 g, 1.15 eq in 15 ml $H_2O$) and the suspension (DCU) stirred overnight under argon at room temperature. The mixture was filtered, partitioned between 1% $KHSO_4$ and EtOAc, the organic phase washed with $H_2O$ (2×), dilute $NaHSO_3$ and brine, then evaporated to an oil. Purification via the adamantanamine salt was achieved by dissolving the crude oil in $Et_2O$ (20 ml) and EtOAc (5 ml) and treating the mixture with an ethereal solution of adamantanamine (1.71 g in 5.0 ml $Et_2O$). Hexane was added and the mixture left overnight to crystallize. Solvent was decanted off and the residual white solid was partitioned between 1.0N HCl and EtOAc to regenerate the acid.

The organic phase was washed with brine, dried over anhydrous $Na_2SO_4$ and evaporated to give 5.043 g (85% for this plus previous step) of title phosphonic acid as a viscous, pale yellow oil with consistent $C^{13}$ NMR spectral data. ($CDCl_3$, 15 MHz). TLC (20:1:1) i-PrOH—$NH_4OH$—$H_2O$, $R_f = 0.37$, UV+PMA.

G. (S)-2-[[Hydroxy(4-phenylbutyl)phosphinyl]oxy]-6-[[(phenylmethoxy)carbonyl]amino]hexanoic acid A solution of Part F methyl ester (5.0 g, 10.2 mM, 1 eq) in dioxane (15 ml) was treated with a 2.0N solution of NaOH (22.4 mmole, 11.2 ml, 2.2 eq) and the mixture stirred under argon at room temperature for 2 hours. The mixture was acidified with concentrated HCl (2 ml) and extracted with EtOAc. The organic phase was washed with brine, dried over anhydrous $Na_2SO_4$ and evaporated to give 4.8 g (99%) of title free acid as a clear, colorless viscous oil with consistent $C^{13}$ NMR spectral data ($CDCl_3$, 15 MHz). TLC (20:1:1) $CH_2Cl_2$-HOAc-$CH_3OH$, $R_f = 0.10$, UV+PMA.

H. N-Cyclohexylglycine, Phenylmethyl Ester

A mixture of cyclohexylamine (9.5 ml, 83 mmole, 1.1 eq) and $Et_3N$ (12.5 ml, 90 mmole, 1.2 eq) in $Et_2O$ (60 ml) at 0° C. (ice bath) was treated dropwise with a solution of benzyl bromoacetate (11.9 ml, 75 mmole, 1 eq) in $Et_2O$ (30 ml). Upon completed addition the mixture was warmed to room temperature and stirred overnight under argon. The suspension was filtered, evaporated to a brown oil and purified by flash chromatography on LPS-1 silica gel eluting with (3:2) Hex-$Et_2O$. Product fractions were evaporated to a clear oil which was dissolved in $Et_2O$ (25 ml) and added by pipette portions to a cooled, (0° C.) HCl saturated $Et_2O$ solution (100 ml). Precipitated salt was collected by filtration and washed with $Et_2O$ to give 9.215 g (44%) of title amine•HCl as a white solid with consistent $C^{13}$ NMR spectral data ($CDCl_3$, 15 MHz). TLC (1:1) $Et_2O$-Hex, $R_f = 0.23$, UV+PMA.

I. (S)-N-[2-[[Hydroxy(4-phenylbutyl)phosphinyl]oxy]-1-oxo-6-[[(phenylmethoxy)carbonyl]amino]hexyl]-N-cyclohexylglycine, phenylmethyl ester A mixture of Part G phosphonic acid (1.040 g, 2.18 mmole, 1.0 eq) and Part H amine•HCl (925 mg, 3.27 mmole, 1.5 eq) in dry THF (20 ml) and $Et_3N$ (0.46 ml, 1.5 eq) was treated with excess N,N-dicyclohexylcarbonyldiimide (DCC) (1.155 g, 2.5 eq) and stirred for 6 hours at room temperature under argon. The suspension was diluted with EtOAc, precipitated DCU filtered off, the filtrate washed with 5% $KHSO_4$, saturated $NaHCO_3$ and brine, then dried over anhydrous $Na_2SO_4$ and evaporated to an oil. Nonpolar impurities were removed by chromatography on a 1″ pad of LPS-1 silica gel eluting with neat $CH_2Cl_2 \rightarrow (8:2)$ $CH_2Cl_2$-Acetone$\rightarrow (8:2)$ $CH_2Cl_2$—$CH_3OH$. Product fractions were evaporated to give 800 mg (52%) of coupled title phosphonic acid as a pale, yellow glass with consistent $C^{13}$ NMR spectral data ($CDCl_3$, 15 MHz). TLC (7:2:1) i-PrOH-$NH_4OH$-$H_2O$, $R_f = 0.72$, UV+PMA.

J. (S)-N-[6-Amino-2-[[hydroxy(4-phenylbutyl)phosphinyl]oxy]-1-oxohexyl]-N-cyclohexylglycine, dilithium salt An argon purged solution of the Part I di-ester (800 mg) in $CH_3OH$ (20 ml) was treated with 20% $Pd(OH)_2$/C (120 mg, 15% by weight) and the black suspension stirred under $H_2$ for 3 hours. Catalyst was removed by filtration through dry, packed Celite and the filtrate evaporated. The residue was taken up in 1.0N LiOH (5 ml) and filtered through a polycarbonate membrane to remove traces of DCU. The filtrate was evaporated, taken up in 5 ml $H_2O$ and chromatographed on HP-20 resin eluting with a neat $H_2O \rightarrow$ neat $CH_3CN$ linear gradient. Product fractions were filtered through a polycarbonate membrane, evaporated, taken up in $H_2O$ (50 ml), frozen and lyophilized to give 421 mg (69%) of desired title acid as a white, hydrated dilithium salt with consistent $C^{13}$ NMR ($D_2O$, Dioxane ref., 15 MHz) spectral data. TLC (7:2:1) i-PrOH-$NH_4OH$-$H_2O$, $R_f = 0.29$, UV+PMA.

Anal Calcd for $C_{24}H_{37}N_2O_6PLi_2$•2.40 moles $H_2O$: C, 53.61; H, 7.84; N, 5.21; P, 5.76. Found: C, 53.69; H, 8.02; N, 5.27; P, 5.50.

EXAMPLE 138

N-[(S)-6-Amino-2-[[hydroxy(4-phenylbutyl)phosphinyl]oxy]-1-oxohexyl]-L-phenylalanine, dilithium salt

A.

N-[(S)-2-[[Hydroxy(4-phenylbutyl)phosphinyl]oxy]-1-oxo-6-[[(phenylmethoxy)carbonyl]amino]hexyl]-L-phenylalanine, benzyl ester A cooled (0° C., ice bath) solution of Example 1, Part G phosphonic ester (1.157 g, 2.42 mmole, 1.0 eq) in dry THF (15 ml) was treated with 1,1-carbonyldiimidazole (CDI) (471 mg, 2.90 mm, 1.2 eq) and the mixture stirred under argon at 0° C. for 1 hour. Phenylalanine benzyl ester.p-TsOH (1.24 g, 2.90 mmole, 1.2 eq, commercially available from Sigma Chem. Co.) and Et$_3$N (0.74 ml, 5.32 mmole, 2.2 eq) were added and the white suspension stirred at room temperature overnight. The mixture was partitioned between 1.0N HCl and EtOAc, the organic phase washed with saturated NaHCO$_3$, 1.0N HCl and brine then dried over anhydrous Na$_2$SO$_4$ and evaporated to give 1.744 g (99%) of desired title dipeptide plus a minor nonpolar impurity as a white solid with consistent $^{13}$C NMR spectra data. (CDCl$_3$, 15 MHz). TLC (9:1) CH$_2$Cl$_2$-CH$_3$OH, R$_f$=0.22 UV+-PMA.

B.

N-[(S)-6-Amino-2-[[hydroxy(4-phenylbutyl)phosphinyl]oxy]-1-oxohexyl]-L-phenylalanine, dilithium salt 20% Pd(OH)$_2$/C (258 mg, 15% by weight) was added to an argon purged solution of the Part A diester (1.720 g) in CH$_3$OH (20 ml) and the black suspension stirred under H$_2$ for 2.0 hours. Catalyst was removed by filtration through a ¼" pad of dry, packed Celite and the filtrate evaporated to a clear oil. The crude oil was dissolved in 1.0N LiOH (4.0 ml) and chromatographed on HP-20 resin eluting with a neat H$_2$O→neat CH$_3$CN linear gradient. Product fractions were evaporated, taken up in H$_2$O (50 ml), filtered through a polycarbonate membrane (0.4 μm), frozen and lyophilized to give 872 mg (66% based on weight of hydrate) of title diacid as the hydrated white dilithium salt with consistent $^{13}$C NMR (D$_2$O, dioxane ref., 15 MHz) spectral data. TLC (7:2:1) i-PrOH-NH$_4$OH-H$_2$O, R$_f$=0.44, UV+PMA.

Anal Calcd for C$_{25}$H$_{33}$N$_2$O$_6$PLi$_2$+1.25 moles H$_2$O: C, 57.20; H, 6.82; N, 5.34; P. 5.90. Found: C, 57.25; H, 6.87; N, 5.40; P. 5.60.

EXAMPLE 139

3-[(S)-6-Amino-2-[hydroxy(4-phenylbutyl)phosphinyl]oxy]-1-oxohexyl]-4-thiazolidine carboxylic acid, dilithium salt

A.

(S)-[[(Trifluoromethyl)carbonyl]amino]-2-hydroxyhexanoic acid, phenylmethyl ester A suspension of the Example 137, Part A hydroxy amino acid (4.50 gm, 30.6 mmole) in dry acetonitrile (60 ml) was treated with excess bis(trimethylsilyl)trifluoroacetamide (24.0 ml) and stirred at room temperature under argon for 2 hours. The resulting clear solution was cooled in an ice bath, treated with trifluoroacetic anhydride (5.25 ml, 37.2 mmole) and allowed to warm to room temperature. The mixture was concentrated on the rotovap, the residue taken up in CH$_3$CN (~50 ml), treated with water (~10 ml) and stirred at room temperature for 30 minutes. The mixture was evaporated to dryness, the residue taken up in half-saturated NaHCO$_3$ solution and washed (2×) with Et$_2$O. The aqueous phase was acidified with concentrated HCl, saturated with solid NaCl and extracted with EtOAc. The EtOAc extract was washed with saturated NaCl solution, dried over Na$_2$SO$_4$ and evaporated. The residue was triturated with hexane to give the crude N-trifluoroacetyl amino acid (7.414 gm, 100%) as a white solid. TLC (AcOH—MeOH—CH$_2$Cl$_2$; 1:1:20) R$_f$=0.28.

The crude acid (7.414 gm) was dissolved in dry DMF (30 ml), treated with benzyl bromide (3.95 ml, 33.2 mmole) and powdered potassium bicarbonate (3.35 gm, 33.5 mmole) and stirred at room temperature under argon. After 5 hours, the mixture was partitioned between EtOAc—water (~100 ml each). The organic phase was washed with water (2×, 50 ml) and saturated NaCl solution, dried over Na$_2$SO$_4$ and evaporated. Trituration of the crude product with hexane gave the title benzyl ester (9.44 gm, 93% overall) as a white crystalline solid, m.p. 60°-61° C. alpha$_D$=12.4° (c=1.25, MeOH). TLC (acetone-CH$_2$Cl$_2$; 15:85) R$_f$=0.50.

B.

(S)-2-[[Hydroxy(4-phenylbutyl)phosphinyl]oxy]-6-[[(trifluoromethyl)carbonyl]amino]hexanoic acid, benzyl ester A solution of the Part A benzyl ester (9.24 gm, 27.7 mmole) and 4-phenylbutylphosphonous acid (8.30 gm, 41.9 mmole) in dry THF (60 ml) at 0° C. (ice bath) under argon was treated with N,N-dicyclohexylcarbodiimide (8.57 gm, 41.6 mmole) and 4-(N,N-dimethylamino)pyridine (1.00 gm, 8.20 mmole) and allowed to warm to room temperature. After stirring at room temperature for 2 hours, the mixture was filtered, diluted with EtOAc (~150 ml) and washed successively with 5% KHSO$_4$, saturated NaHCO$_3$ and saturated NaCl solutions, dried over Na$_2$SO$_4$ and evaporated. TLC (acetone-Et$_2$O; 2:8) R$_f$=0.60 (R$_f$ of Part A benzyl ester=0.69).

The crude phosphonous mono ester was taken up in dioxane (80 ml), treated with a solution of NaIO$_4$ (6.89 gm, 32.2 mmole) in water (40 ml) and stirred at room temperature under argon for 18 hours. The mixture was then partitioned between EtOAc-1% KHSO$_4$ solution (~150 ml each), the organic phase washed successively with water, dilute NaHSO$_3$ and saturated NaCl solutions, dried over Na$_2$SO$_4$ and evaporated to give the crude title phosphonic acid (16.04 gm, theory 14.68 gm) as a pale yellow, viscous oil suitable for use in the next step. TLC (AcOH—MeOH—CH$_2$Cl$_2$; 1:1:20) R$_f$=0.22.

C.

(S)-2-[[Hydroxy(4-phenylbutyl)phosphinyl]oxy]-6-[[(trifluoromethyl)carbonyl]amino]hexanoic acid The crude Part B phosphonic acid (16.04 gm, theory 14.68 gm) was taken up in methanol (75 ml)—water (7.5 ml), treated with 10% Pd-C (1.00 gm) and hydrogenated in a Parr apparatus at 30 psi for 2 hours. The catalyst was removed by filtration through Celite and the filtrate evaporated to dryness. The residue was taken up in half-saturated NaHCO$_3$ (~75 ml) and washed with EtOAc. The aqueous phase was acidified with concentrated HCl and extracted with EtOAc. The EtOAc extract was washed with saturated NaCl, dried over Na$_2$SO$_4$ and evaporated to give the title diacid. TLC (AcOH—MeOH—CH$_2$Cl$_2$; 1:1:8) showed major product at R$_f$=0.32.

D.
3-[(S)-[[(Trifluoromethyl)carbonyl]amino]-2-[hydroxy(4-phenylbutyl)phosphinyl]oxy]-1-oxohexyl]-4-thiazolidine carboxylic acid, methyl ester A cooled (0° C., ice bath) mixture of Part C phosphonic acid (836 mg, 1.90 mmole) in dry THF (10 ml) was treated with N,N-carbonyldiimide (373 mg, 2.28 mmole, 1.2 eq) and stirred for one hour under argon at 0° C. 4-Thiazolidine carboxylic acid, methyl ester, hydrochloride (Ref. Ratner, S. et al, JACS, Vol. 59, p. 203 (1937)) (422 mg, 2.3 mmole, 1.2 eq) and Et$_3$N (0.32 ml, 2.3 mmole, 1.2 eq) were added and the resulting suspension stirred overnight under argon at room temperature. The reaction mixture was partitioned between 5% KHSO$_4$ and EtOAc, the organic phase washed with saturated NaHCO$_3$ and brine, then dried over anhydrous Na$_2$SO$_4$ and evaporated to an oil semi-solid. The material was slurried in CH$_3$CN, filtered and evaporated to give 829 mg (80.5%) of desired title coupled product as an oil with consistent C$^{13}$ NMR spectral data (CD$_3$CN, 15 MHz). TLC (20:1:1) CH$_2$Cl$_2$—CH$_3$OH—HOAc, R$_f$ 0.21, UV+PMA.

E.
3-[(S)-6-Amino-2-[hydroxy(4-phenylbutyl)phosphinyl]oxy-1-oxohexyl]-4-thiazolidine carboxylic acid, dilithium salt A solution of Part A diester (829 mg, 1.53 mM) in dioxane (12 ml) was treated with 1.0N LiOH (7.7 ml, 7.7 mM, 5.0 eq) and the clear mixture stirred for 1.5 hours under argon at room temperature. The reaction mixture was diluted with H$_2$O, extracted once with EtOAc, the aqueous phase filtered through a polycarbonate membrane (0.4 μm) and concentrated to a 5.0 ml volume. The crude aqueous solution was chromatographed on HP-20 resin eluting with a neat H$_2$O to neat CH$_3$CN linear gradient system. Product fractions were combined, evaporated, taken up in H$_2$O (50 ml), filtered through a polycarbonate membrane, frozen, and lyophilized to give 436 mg (57.3% based on weight of hydrate) of desired title di-lithium salt as a fluffy, white powder with consistent C$^{13}$ NMR spectral date (D$_2$O, dioxane ref., 15 MHz). TLC (7:2:1), i-PrOH-NH$_4$OH-H$_2$O, R$_f$=0.25, UV+PMA.

What is claimed is:

1. A compound of the formula $$R_1-\overset{O}{\underset{OR_3}{\overset{\|}{P}}}-O-\overset{R_2}{\underset{}{\overset{|}{C}H}}-\overset{O}{\overset{\|}{C}}-X$$

and pharmaceutically acceptable salts thereof wherein: X is $$\begin{array}{c} R_9 \quad S \quad R_{10} \\ R'_9-\!\!\!\!+\!\!\!\!\!\!\quad\!\!\!\!+\!\!\!\!-R'_{10} \\ -N\!\!\rule{1.5em}{0.4pt}\!\!C-COOR_6 \text{ or } -N-CH-COOR_6; \\ \quad |\quad\quad | \quad\quad\quad\quad\quad\quad\quad | \quad | \\ \quad H \quad (L) \quad\quad\quad\quad\quad\quad R_{21} \; R_{22} \end{array}$$

R$_9$, R'$_9$, R$_{10}$ and R'$_{10}$ are independently selected from hydrogen and lower alkyl or R'$_9$, R$_{10}$, R'$_{10}$ are hydrogen and R$_9$ is —⟨phenyl⟩—(R$_{12}$)$_p$ ;

R$_{11}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl;

R$_{12}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy;

m is zero, one, two or three;

p is one, two or three provided that p is more than one only if R$_{11}$ or R$_{12}$ is hydrogen, methyl, methoxy, chloro, or fluoro;

R$_{21}$ is hydrogen, lower alkyl, cycloalkyl, phenyl or

—(CH$_2$)$_r$—⟨phenyl⟩ ;

R$_{22}$ is hydrogen, lower alkyl,

—(CH$_2$)$_r$—⟨phenyl⟩ , —(CH$_2$)$_r$—⟨phenyl⟩—OH,

—(CH$_2$)$_r$—⟨phenyl⟩—OH, —(CH$_2$)$_r$—⟨indole⟩ ,
        |
        OH

—(CH$_2$)$_r$—⟨imidazole⟩—N, —(CH$_2$)$_r$—NH$_2$, —(CH$_2$)$_r$—SH,

—(CH$_2$)$_r$—S—lower alkyl, —(CH$_2$)$_r$—NH—C⟨=NH, NH$_2$⟩ or

—(CH$_2$)$_r$—C(=O)—NH$_2$;

r is an integer from 1 to 4;
R$_1$ is alkyl of 1 to 10 carbons, aminoalkyl, haloalkyl, —(CH$_2$)$_q$—⟨phenyl⟩—(R$_{11}$)$_p$ , —(CH$_2$)$_q$—cycloalkyl, —(CH$_2$)$_q$—⟨thiophene⟩ , —(CH$_2$)$_q$—⟨furan⟩ , -continued

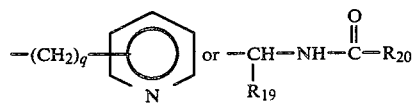

wherein q is zero or an integer from 1 to 7; and $R_{11}$ and p are as defined above; and
$R_{19}$ and $R_{20}$ are independently selected from the group consisting of hydrogen, lower alkyl, halo substituted lower alkyl,

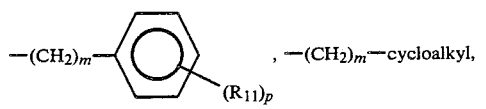

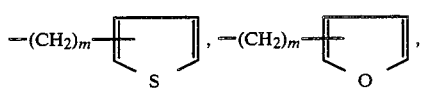

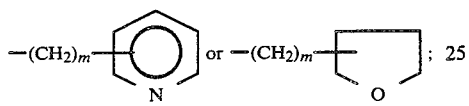

wherein m, $R_{11}$ and p are as defined above;
$R_2$ is hydrogen, lower alkyl, halo substituted lower alkyl,

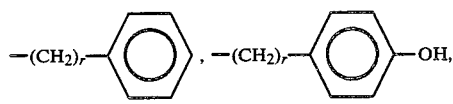

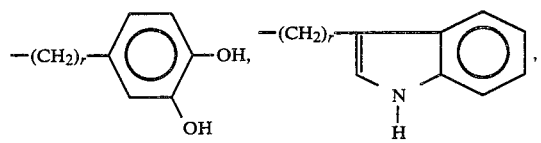

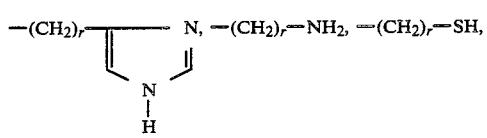

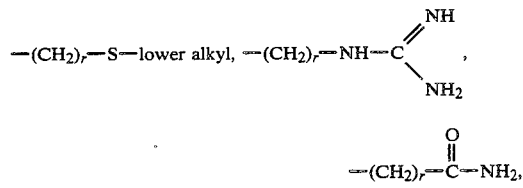

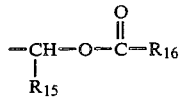

wherein r is as defined hereinbefore;
$R_3$ and $R_6$ are independently selected from hydrogen, lower alkyl, benzyl, benzhydryl, alkali metal or $$-\underset{R_{15}}{\underset{|}{CH}}-O-\overset{O}{\overset{\|}{C}}-R_{16}$$

wherein $R_{15}$ is hydrogen, lower alkyl, cycloalkyl, or phenyl, and $R_{16}$ is hydrogen, lower alkyl, lower alkoxy, phenyl, or $R_{15}$ and $R_{16}$ taken together are $-(CH_2)_2-$, $-(CH_2)_3$, $-CH=CH-$ or

2. A compound of claim 1 wherein:
$R_9$, $R'_9$, $R_{10}$ and $R'_{10}$ are all hydrogen, or $R_9$ is phenyl, 2-hydroxyphenyl or 4-hydroxyphenyl and $R'_9$, $R_{10}$ and $R'_{10}$ are hydrogen;
m is zero, one or two;
$R_{11}$ is hydrogen, methyl, methoxy, methylthio, chloro, bromo, fluoro, or hydroxy;
$R_2$ is hydrogen, lower alkyl or 1 to 4 carbons, $CF_3$, or amino substituted lower alkyl of 1 to 4 carbons;
$R_1$ is alkyl of 1 to 10 carbons,

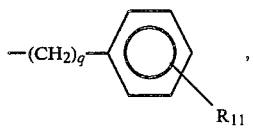

$-(CH_2)_q$-cycloalkyl wherein cycloalkyl is of 5 or 6 carbons,

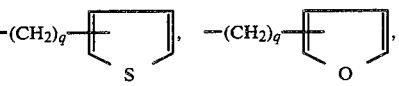

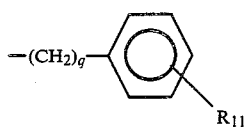

wherein q is zero or an integer from 1 to 4 and $R_{11}$ is as defined above;
$R_{19}$ and $R_{20}$ are independently selected from lower alkyl of 1 to 4 carbons or

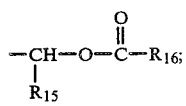

wherein q and $R_{11}$ are as defined above;
$R_3$ and $R_6$ are independently selected from hydrogen, alkali metal salt, lower alkyl of 1 to 4 carbons, or $$-\underset{R_{15}}{\underset{|}{CH}}-O-\overset{O}{\overset{\|}{C}}-R_{16};$$

$R_{15}$ is hydrogen, methyl or isopropyl; and
$R_{16}$ is lower alkyl of 1 to 4 carbons or phenyl.
3. A compound of claim 2 wherein X is

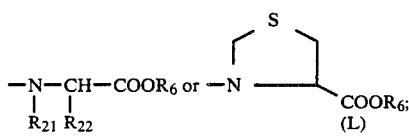

m is zero, one or two;
R₁₁ is hydrogen, methyl, methoxy, methylthio, bromo, fluoro, or hydroxy;
and R₆ is hydrogen,

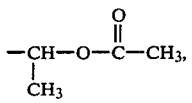

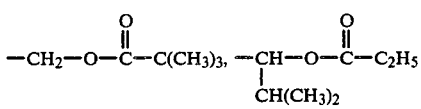

or an alkali metal salt;
R₁ is

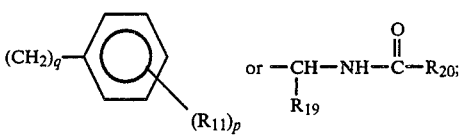

R₂₁ is cycloalkyl or H, R₂₂ is H or benzyl;
R₂ is hydrogen or lower alkyl; and R₃ is hydrogen, alkali metal or benzyl.

4. A compound of claim 1 wherein
R₁ is phenylalkyl or

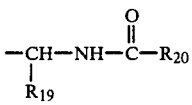

wherein R₁₉ is phenylalkyl and R₂₀ is phenyl;
R₂ is hydrogen, methyl, or —(CH₂)₄—NH₂; and
R₃ is hydrogen, phenylmethyl,

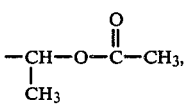

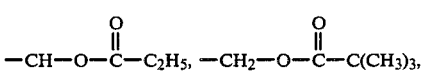

or an alkali metal CH(CH₃)₂ salt.

5. A compound of claim 2 wherein R₁ is alkyl of 1 to 10 carbons.

6. A compound of claim 5 wherein X is

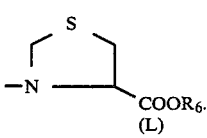

7. The compound of claim 3 wherein R₁ is phenylbutyl; R₂ is methyl; and R₃ and R₆ are an alkali metal salt.

8. The compound of claim 2 wherein R₁ is

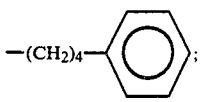

R₂ is methyl; R₃ is ethyl; and R₆ is an alkali metal salt.

9. The compound of claim 2 wherein R₁ is

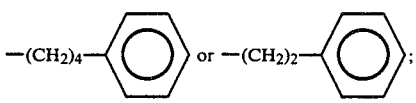

R₂ is methyl; R₃ is

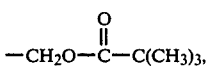

and R₆ is an alkali metal salt.

10. The compound of claim 6 wherein R₁ is

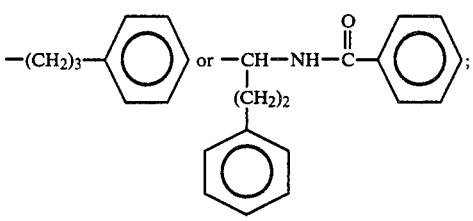

R₂ is methyl; and R₃ and R₆ are an alkali metal salt.

11. The compound of claim 6 wherein R₁ is

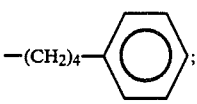

R₂ is hydrogen; and R₃ and R₆ are an alkali metal salt.

12. The compound of claim 7 wherein R₁ is

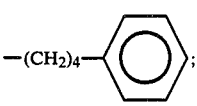

R₂ is methyl; and R₃ and R₆ are an alkali metal salt.

13. The compound of claim 1 wherein R₁ is

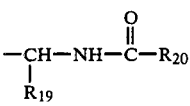

and R₁₉ and R₂₀ are independently selected from lower alkyl of 1 to 4 carbons or

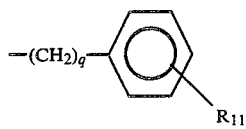

wherein q is zero or an integer from 1 to 4 and $R_{11}$ is hydrogen, methyl, methoxy, methylthio, chloro, bromo, fluoro, or hydroxy.

14. The compound of claim 2 wherein $R_{21}$ is hydrogen, methyl, phenyl, cyclopentyl or cyclohexyl;

$R_{22}$ is hydrogen, lower alkyl of 1 to 4 carbons,

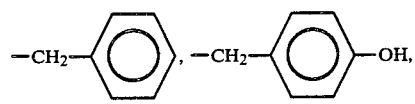

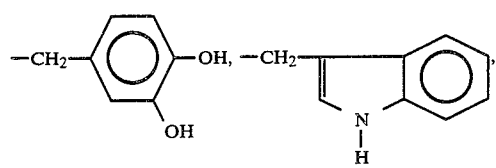

$-(CH_2)_4-NH_2, -CH_2SH, -(CH_2)_2-S-CH_3,$

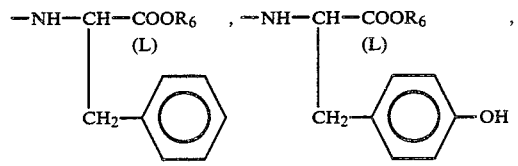

15. A compound of claim 14 wherein X is

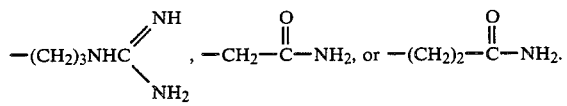

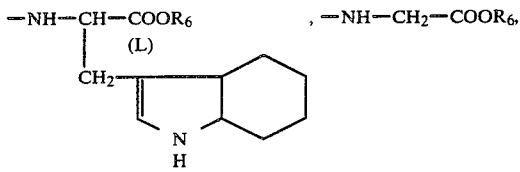

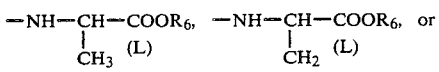

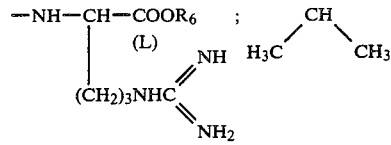

and $R_6$ is hydrogen,

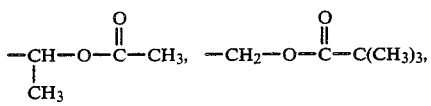

or an alkali metal salt.

16. The compound of claim 1 having the name (S)-N-[6-amino-2-[[hydroxy(4-phenylbutyl)phosphinyl]oxy]-1-oxohexyl]-N-cyclohexylglycine, or its dilithium salt.

17. The compound of claim 1 having the name N-[(S)-6-amino-2-[[hydroxy(4-phenylbutyl)phosphinyl]oxy]-1-oxohexyl]-L-phenylalanine or its dilithium salt.

18. The compound of claim 1 having the name 3-[(S)-6-amino-2-[hydroxy(4-phenylbutyl)phosphinyl]oxy]-1-oxohexyl]-4-thiazolidine carboxylic acid, or its dilithium salt.

19. A composition useful for treating hypertension comprising a pharmaceutically acceptable carrier and an effective amount of a hypotensive agent or pharmaceutically acceptable salt thereof of the formula

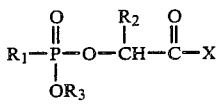

wherein X, $R_1$, $R_2$ and $R_3$ are as defined in claim 1.

20. The composition of claim 20 also including a diuretic.

21. The method of alleviating hypertension in a mammalian specie which comprises administering an effective amount of the composition of claim 20.

* * * * *